United States Patent
Holtcamp et al.

(10) Patent No.: US 8,809,563 B2
(45) Date of Patent: *Aug. 19, 2014

(54) METATHESIS CATALYST AND PROCESS FOR USE THEREOF

(75) Inventors: Matthew W. Holtcamp, Huffman, TX (US); Catherine A. Faler, Houston, TX (US); Caol P. Huff, Houston, TX (US); Matthew S. Bedoya, Humble, TX (US); John R. Hagadorn, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/535,875

(22) Filed: Jun. 28, 2012

(65) Prior Publication Data

US 2012/0289729 A1   Nov. 15, 2012

Related U.S. Application Data

(63) Continuation-in-part of application No. 12/705,136, filed on Feb. 12, 2010, now Pat. No. 8,237,003.

(60) Provisional application No. 61/259,521, filed on Nov. 9, 2009, provisional application No. 61/259,514, filed on Nov. 9, 2009.

(51) Int. Cl.
*C07F 15/00* (2006.01)
*C07C 1/22* (2006.01)

(52) U.S. Cl.
USPC ............................. 556/22; 585/639

(58) Field of Classification Search
CPC ...... C07C 6/04; C07C 11/02; C07C 2631/22; C07C 11/00; C07C 67/333; C07C 207/06; C07C 15/0046; C07C 15/002; C10G 2300/1014; C10G 2300/1088; C10G 2400/22; C10G 3/44; C10G 2300/4025
See application file for complete search history.

(56) References Cited

U.S. PATENT DOCUMENTS

| | | | |
|---|---|---|---|
| 4,545,941 A | 10/1985 | Rosenburg | |
| 6,900,347 B2 | 5/2005 | Paulson et al. | |
| 7,119,216 B2 | 10/2006 | Newman et al. | |
| 7,205,424 B2 | 4/2007 | Nolan | |
| 7,268,242 B2 | 9/2007 | Pederson et al. | |
| 7,312,331 B2 | 12/2007 | Bertrand et al. | |
| 7,632,772 B2 | 12/2009 | Zhan | |
| 2005/0070750 A1 | 3/2005 | Newman et al. | |
| 2006/0287450 A1 | 12/2006 | Kohler et al. | |
| 2007/0043180 A1 | 2/2007 | Zhan | |
| 2007/0270621 A1 | 11/2007 | Millis et al. | |
| 2008/0027194 A1 | 1/2008 | Schrodi | |
| 2008/0064891 A1 | 3/2008 | Lee | |
| 2008/0269525 A1 | 10/2008 | Bertrand et al. | |
| 2009/0048459 A1 | 2/2009 | Tupy et al. | |
| 2009/0069516 A1 | 3/2009 | Obrecht et al. | |
| 2009/0187035 A1 | 7/2009 | Ko et al. | |
| 2009/0259065 A1 | 10/2009 | Abraham et al. | |
| 2010/0022789 A1 | 1/2010 | Mignani et al. | |
| 2010/0174068 A1 | 7/2010 | Grela et al. | |
| 2011/0112349 A1 | 5/2011 | Holtcamp et al. | |

FOREIGN PATENT DOCUMENTS

| | | |
|---|---|---|
| EP | 2 151 446 | 2/2010 |
| JP | 58-154594 | 9/1983 |
| KR | 10-2009-0024737 | 3/2009 |
| WO | WO 00/71554 | 11/2000 |
| WO | WO 2004/062763 | 7/2004 |
| WO | WO 2006/138166 | 12/2006 |
| WO | 2008-000644 | 1/2008 |
| WO | WO 2008/010961 | 1/2008 |
| WO | WO 2008/046106 | 4/2008 |
| WO | WO 2008/095785 | 8/2008 |
| WO | WO 2008/125568 | 10/2008 |
| WO | WO 2008/140468 | 11/2008 |
| WO | WO 2009/009597 | 1/2009 |
| WO | WO 2009/126831 | 10/2009 |
| WO | 2011-119778 | 9/2011 |

OTHER PUBLICATIONS

Alder et al., "*Complexation of Stable Carbenes with Alkali Metals*", Chemical Communications, 1999, No. 3, pp. 241-242.
Allen et al., "*Well-Defined Silica-Supported Olefin Metathesis Catalysts*", Organic Letters, 2009, vol. 11, No. 6, pp. 1261-1264.
Anderson et al., "*Kinetic Selectivity of Olefin Metathesis Catalysts Bearing Cyclic (Alkyl)(amino)Carbenes*", Organometallics, 2008, vol. 27, No. pp. 563-566.
Anderson et al., "*Synthesis and Reactivity of Olefin Metathesis Catalysts Bearing Cyclic (Alkyl)(Amino)Carbenes*", Angew. Chem. Int. Ed., 2007, vol. 46, No. 38, pp. 7262-7265.
Arduengo III et al., "*Carbene-Lithium Interactions*", Chemistry Letters, 1999, vol. 28, No. 10, pp. 1021-1022.
Arduengo et al., "*Carbene Adducts of Magnesium and Zinc*", Journal of Organometallic Chemistry, 1993, vol. 462, No. 1-2, pp. 13-18.
Arduengo et al., "*Adducts of Carbenes with Group II and XII Metallocenes*", Organometallics, 1998, vol. 17, No. 15, pp. 3375-3382.
Arnold et al., "*Magnesium and Zinc Complexes of Functionalised, Saturated N-heterocyclic Carbene Ligands: Carbene Lability and Functionalisation and Lactide Polymerisation Catalysis*", Journal of Chemical Society, Dalton Transactions, 2009, No. 35, pp. 7236-7247.
Arnold et al., "*Asymmetric Lithium(I) and Copper (II) Alkoxy-N-Heterocyclic Carbene Complexes: Crystallographic Characterisation and Lewis Acid Catalysis*", Chemical Communications, 2004, pp. 1612-1613.

(Continued)

*Primary Examiner* — Yun Qian
(74) *Attorney, Agent, or Firm* — Catherine L. Bell

(57) ABSTRACT

This invention relates to a Group 8 metal containing catalyst compound for the metathesis of olefins.
This invention also relates to process to make alphaolefins comprising contacting an olefin, such as ethylene, with a feed oil containing a triacylglyceride (typically a fatty acid ester (such as methyl oleate)) with a Group 8 metal containing catalyst compound. The fatty acid ester may be a fatty acid methyl ester derived from biodiesel.

38 Claims, 1 Drawing Sheet

(56) References Cited

OTHER PUBLICATIONS

Arnold et al., "*Anionic Amido N-Heterocyclic Carbenes: Synthesis of Covalently Tethered Lanthanide-Carbene Complexes*", Angewandte Chemie, International Edition, 2003, vol. 42, pp. 5981-5984.

Arrowsmith et al., "*A Hydride-Rich Magnesium Cluster*", Angewandte Chemie, International Edition, 2009, vol. 48, No. 22, pp. 4013-4016.

Azizoglu et al., "*Substituent Effects on the Ring-Opening Mechanism of Lithium Bromocyclopropylidenoids to Allenes*", Journal of Organic Chemistry, 2008, vol. 73, No. 21, pp. 8182-8188.

Berthelot et al., "*Gas-Phase Reactivity of ($C_5H_5Mg$)+ Complexes: An Experimental and Theoretical Study*", Journal of Physical Chemistry, 1998, vol. 102, No. 29, pp. 6025-6034.

Blum et al., "*Synthesis of N-Heterocyclic Carbene-Containing Metal Complexes from 2-(Pentaflurophenl)Imidazolidines*", Organometallics, 2007, vol. 26, No. 8, pp. 2122-2124.

Bourisson et al., "*Stable Carbenes*", Chemical Reviews, 2000, vol. 100, No. 1, pp. 39-91.

Burdett et al., "*Renewable Monomer Feedstocks via Olefin Metathesis: Fundamental Mechanistic Studies of Methyl Oleate Ethenolysis with the First-Generation Grubbs Catalyst*", Organometallics, 2004, vol. 23, No. 9, pp. 2027-2047.

Chung et al., "*Olefin Metathesis Catalyst: Stabilization Effect of Backbone Substitutions of N-Heterocyclic Carbene*", Organic Letters, 2008, vol. 10, No. 13, pp. 2693-2696.

De Fremont et al., "*Cationic NHC-Gold(I) Complexes: Synthesis, Isolation and Catalytic Activity*", Journal of Organometallic Chemistry, 2009, vol. 694, pp. 551-560.

Diez-Gonzalez et al., "*N-Heterocyclic Carbenes in Late Transition Metal Catalysts*", Chemical Reviews, 2009, vol. 109, No. 8, pp. 3612-3676.

Dinger et al., "*Adamantyl-Substituted N-Heterocyclic Carbene Ligands in Second-Generation Grubbs-Type Metathesis Catalysts*", Organometallics, 2003, vol. 22, No. 25, pp. 5291-5296.

Dragutan et al., "*Ruthenium Indenylidene Complexes: Metathesis Catalysts With Enhanced Activity*", Platinum Metals Rev., 2005, vol. 49, No. 1, pp. 33-40.

Fraenkel et al., "*A Homopletic Carbene-Lithium Complex*", Angewandte Chemie, International Edition, 2001, vol. 40, No. 10, pp. 1907-1910.

Furstner et al., "*Ruthenium Carbene Complexes with N,N'-Bis(mesityl)imidazol-2-ylidene Ligands: RCM Catalysts of Extended Scope*", J. Org. Chem., 2000, vol. 65, No. 7, pp. 2204-2207.

Hahn et al., "*Heterocyclic Carbenes: Synthesis and Coordination Chemistry*", Angewandte Chemie International Edition, 2008, vol. 47, pp. 3122-3172.

Hermann et al., "*Heterocyclic Carbenes: A High-Yielding Synthesis of Novel, Functionalized N-Heterocyclic Carbenes in Liquid Ammonia*", Chemistry, A European Journal, 1996, vol. 2, No. 12, pp. 1627-1636.

Herrmann et al., "*N-Heterocyclic Carbenes[+]: Generation under Mild Conditions and Formation of Groups 8-10 Transition Metal Complexes Relevant to Catalysts*", Chemistry, A European Journal, 1996, vol. 2, No. 7, pp. 772-780.

Hoveyda et al., "*A Recyclable Ru-Based Metathesis Catalyst*", Journal of American Chemical Society, 1999, vol. 121, pp. 791-799.

Jazzar et al., "*Intramolecular 'Hydroiminiumation' of Alkenes: Applications to the Synthesis of Conjugate Acids of Cyclic Alkyl Amino Carbenes (CAACs)*", Angew. Chem. Int. Ed., 2007, vol. 46, No. 16, pp. 2899-2902.

Jazzar et al., A New Synthetic Method for the Preparation of Protonated-NHCs and Related Compounds, J. Organometallic Chemistry 691, 2006, No. 14, pp. 3201-3205.

Kingsbury et al., "*A Recyclable Ru-Based Metathesis Catalyst*", J. Am. Chem. Soc., 1999, vol. 121, pp. 791-799.

Lavallo et al., "*A Rigid Cyclic (Alkyl)(Amino)carbene Ligand Leads to Isolation of Low-Coordinate Transition Metal Complexes*", Angew. Chem. Int. Ed., 2005, vol. 44, No. 44, pp. 7236-7239.

Lavallo et al., "*Stable Cyclic (Alkyl)(Amino)carbenes as Rigid or Flexible, Bulky Electron-Rich Ligands for Transition Metal Catalysts: A Quaternary Carbon Atom Makes the Difference*", Angew. Chem. Int. Ed., 2007, vol. 44, No. 35, pp. 5705-5709.

Lavallo et al., "*Isolation of Cyclopropenylidene-Lithium Adducts: The Weiss-Yoshida Reagent*", Angewandte Chemie, International Edition, 2006, vol. 45, No. 40, pp. 6652-6655.

Ledoux et al., "*Comparative Investigation of Hoveyda-Grubbs Catalysts Bearing Modified N-Heterocyclic Carbene Ligands*", Advanced Synthesis & Catalysis, 2007, vol. 349, No. 10, pp. 1692-1700.

Ledoux et al., "*N-N'-Dialkyl- and N-Alkyl-N-Mesityl-Substituted N-Heterocyclic Carbenes as Ligands in Grubbs Catalysts*", Chemistry, A European Journal, 2006, vol. 12, No. 17, pp. 4654-4661.

Leuthausser et al., "*π-Face Donor Properties of N-Heterocyclic Carbenes in Grubbs II Complexes*", Chemistry, A European Journal, 2008, vol. 14, No. 18, pp. 5465-5481.

Lichtenheldt et al., "*Alternating Ring-Opening Metathesis Copolymerization by Grubbs-Type Initiators with Unsymmetrical N-Heterocyclic Carbenes*", Chemistry, A European Journal, 2009, vol. 15, No. 37, pp. 9451-9457.

Platform Chemicals from an Oilseed Biorefinery, Grant No. DE-FG36-04GO14016 awarded by the Department of Energy, Final Technical Report.

Rybak et al., "*Metathesis as a Versatile Tool in Oleochemistry*", Eur. J. Lipid Sci. Technol., 2008, vol. 110, pp. 797-804.

Santhosh Kumar et al., "*Factors Relevant for the Regioselective Cyclopolymerization of 1,6-Heptadiynes, N,N-Dipropargylamines, N,N-Dipropargylammonium Salts, and Dipropargyl Ethers by RuIV-Alklidene-Based Metathesis Initiators*", Journal of the American Chemical Society, 2009, vol. 131, No. 1, pp. 387-395.

Scholl et al., "*Synthesis and Activity of a new Generation of Ruthenium-Based Olefin Metathesis Catalysts Coordinated with 1,3-Diesityl-4, 5-Dihydroimidazol-2-ylidene Ligands*" Org. Letters, 1999, vol. 1, pp. 953-956.

Schrodi et al., "*Ruthenium Olefin Metathesis Catalysts for the Ethenolysis of Renewable Feedstocks*", Clean: Soil, Air, Water, vol. 36, No. 8, pp. 669-673.

Schumann et al., "*Metallocenes of the Alkaline Earth Metals and Their Carbene Complexes*", Journal of Organometallic Chemistry, 2001, vol. 617-618, pp. 588-600.

Sigal et al., "*Are Disilacyclopropylidenes and Their Carbenoids Good Precursors for the Unknown 1, 3-Disilaallenes?*", Journal of Organometallic Chemistry, 2001, vol. 636, No. 1-2, pp. 148-156.

Stasch et al., "*Synthesis and Characterization of Alkynyl Complexes of Groups 1 and 2*", Chemistry, An Asian Journal, 2009, vol. 4, No. 9, pp. 1451-1457.

Süβner et al., "*π-Face Donor Properties of N-Heterocyclic Carbenes*", Chemical Communications, 2005, No. 43, pp. 5417-5419.

Tamm et al., "*Pentacarbonylkhromium(0) and -tungsten(0) Complexes with the Bis(Diisopropylamino) Cyclopropenylidene Ligand*", Journal of Organometallic Chemistry, 1995, vol. 501, No. 1, pp. 309-313.

Tiede et al., "*Highly Active Chiral Ruthenium-based Metathesis Catalysts Through a Monosubstitution in the N-Heterocyclic Carbene*", Angewandte Chemie, International Edition, 2010, vol. 49, No. 23, pp. 3972-3975.

Vehlow et al., "*Alternating Copolymerizations Using a Grubbs-Type Initiator with an Unsymmetrical, Chiral N-Heterocyclic Carbene Ligand*", Angewandte Chemie, International Edition, 2008, vol. 47, No. 14, pp. 2615-2618.

Vehlow et al., "*Deactivation of Ruthenium Olefin Metathesis Catalysts Through Intromolecular Carbene-Arene Bond Formation*", Angewandte Chemie, International Edition, 2007, vol. 46, No. 42, pp. 8082-8085.

Vehlow et al., "*Ruthenium Metathesis Catalysts with Saturated Unsymmetrical N-Heterocyclic Carbene Ligands*", Organometallics, 2006, vol. 25, No. 1, pp. 25-28.

(56) References Cited

OTHER PUBLICATIONS

Vougioukalakis et al., "*Ruthenium-Based Olefin Metathesis Catalysts Coordinated with Unsymmetrical N-Heterocyclic Carbene Ligands: Synthesis, Structure, and Catalytic Activity*", Chemistry, A European Journal, 2008, vol. 14, No. 25, pp. 7545-7556.

Vougioukalakis et al., "*Ruthenium Olefin Metathesis Catalysts Bearing an N-Fluorophenyl-N-Mesityl-Substituted Unsymmetrical N-Heterocyclic Carbene*", Organometallics, 2007, vol. 26, No. 9, pp. 2469-2472.

Xu et al., "*Development of Building Blocks for the Synthesis of N-Heterocyclic Carbene Ligands*", Organic Letters, 2005, vol. 7, No. 21, pp. 4605-4608.

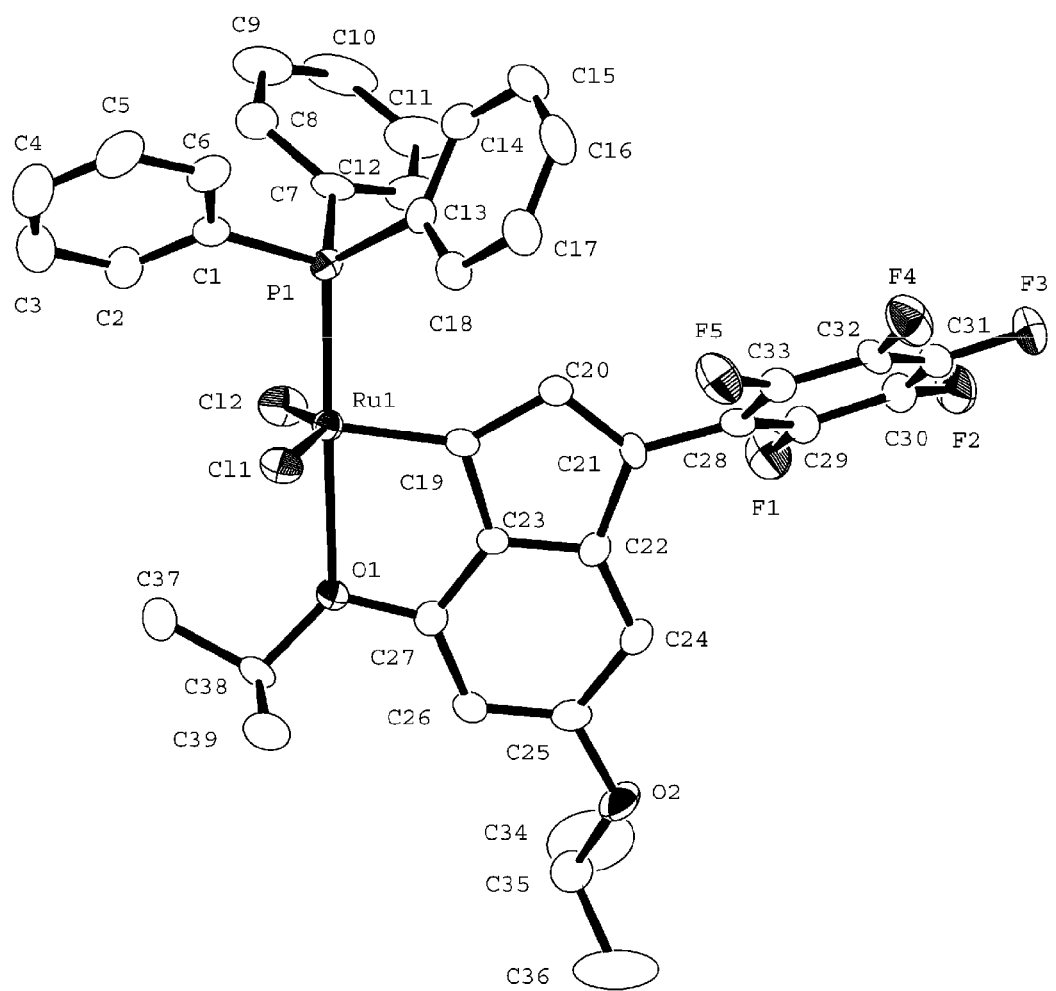

METATHESIS CATALYST AND PROCESS FOR USE THEREOF

PRIORITY

This invention is a continuation-in-part of U.S. Ser. No. 12/705,136, filed Feb. 12, 2010 now U.S. Pat. No. 8,237,003.

STATEMENT OF RELATED APPLICATIONS

This invention is related to U.S. Ser. No. 61/259,521, filed Nov. 9, 2009 and U.S. Ser. No. 61/259,514, filed Nov. 9, 2009.

FIELD OF THE INVENTION

This invention relates to olefin metathesis, more particularly, metathesis catalyst compounds and processes for the use thereof

BACKGROUND OF THE INVENTION

The cross-metathesis of two reactant olefins, where each reactant olefin comprises at least one unsaturation site, to produce new olefins which are different from the reactant olefins is of significant commercial importance. The cross-metathesis reaction is usually catalyzed by one or more catalytic metals, usually one or more transition metals.

One such commercially significant application is the cross-metathesis of ethylene and internal olefins to produce alpha-olefins, which is generally referred to as ethenolysis. In particular, the cross-metathesis of ethylene and an internal olefin to produce linear alpha-olefins (LAOs) is of particular commercial significance. LAOs are useful as monomers or comonomers in certain (co)polymers (polyalphaolefins or PAOs) and/or as intermediates in the production of epoxides, amines, oxo alcohols, synthetic lubricants, synthetic fatty acids, and alkylated aromatics. Olefins Conversion Technology™, based upon the Phillips Triolefin Process, is an example of an ethenolysis reaction converting ethylene and 2-butene into propylene. These processes use heterogeneous catalysts, such as tungsten and rhenium oxides, which have not proven effective for internal olefins containing functional groups such as cis-methyl oleate, a fatty acid methyl ester.

Methods for the production of polyalpha-olefins are typically multi-step processes that often create unwanted by-products and waste of reactants and energy. Full range linear alpha-olefins plants are petroleum-based, are inefficient and result in mixtures of oligomerization products that typically yield Schulz-Flory distributions producing large quantities of undesirable materials. In recent years there have been new technologies implemented to produce "on purpose" linear alpha-olefins such 1-hexene and 1-octene through chromium-based selective ethylene trimerization or tetramerization catalysts. Alternatively, 1-octene has been produced via the telomerization of butadiene and methanol. Similar strategies are not currently available for the production of 1-decene.

1-decene is a co-product typically produced in the cross-metathesis of ethylene and methyl oleate. Alkyl oleates are fatty acid esters that can be major components in biodiesel produced by the transesterification of alcohol and vegetable oils. Vegetable oils containing at least one site of unsaturation include canola, soybean, palm, peanut, mustard, sunflower, tung, tall, perilla, grapeseed, rapeseed, linseed, safflower, pumpkin corn and many other oils extracted from plant seeds. Alkyl erucates similarly are fatty acid esters that can be major components in biodiesel. Useful biodiesel compositions are those which typically have high concentrations of oleate and erucate esters. These fatty acid esters preferably have one site of unsaturation such that cross-metathesis with ethylene yields 1-decene as a co-product.

Biodiesel is a fuel prepared from renewable sources, such as plant oils or animal fats. To produce biodiesel, triacylglycerides ("TAG"), the major compound in plant oils and animal fats, are converted to fatty acid alkyl esters ("FAAE," i.e., biodiesel) and glycerol via reaction with an alcohol in the presence of a base, acid, or enzyme catalyst. Biodiesel fuel can be used in diesel engines, either alone or in a blend with petroleum-based diesel, or can be further modified to produce other chemical products.

Cross-metathesis catalysts reported thus far for the ethenolysis of methyl oleate are typically ruthenium-based catalysts bearing phosphine or carbene ligands. Dow researchers in 2004 achieved catalysts turnovers of approximately 15,000 using the $1^{st}$ generation Grubb's catalyst, bis (tricyclohexylphosphine)benzylidene ruthenium(IV) dichloride, (Organometallics 2004, 23, 2027). Researchers at Materia, Inc. have reported turnover numbers up to 35,000 using a ruthenium catalyst containing a cyclic alkyl amino carbene ligand, (WO 2008/010961). These turnovers were obtained with a catalyst reportedly too expensive for industrial consideration due to high costs associated with the catalysts being derived from a low yielding synthesis (See Final Technical Report entitled "Platform Chemicals from an Oilseed Biorefinery" grant number DE-FG36-04GO14016 awarded by the Department of Energy). Additionally, the introduction of chelating isopropoxybenzylidene ligands has led to ruthenium catalysts with improved activities for metathesis reactions (J. Am. Chem. Soc. 1999, 121, 791). However, these ruthenium alkylidene catalysts are usually prepared by the reaction of ruthenium species with diazo compounds. The concerns associated with industrial scale reactions comprising diazo compounds have led to increased efforts to prepare ruthenium alkylidenes via alternate synthetic routes, such as using terminal alkynes or propargyl alcohols.

The synthesis of $RuCl_2(PCy_3)_2$(3-phenylindenylene) has proven useful in providing an easy route to ruthenium alkylidenes which avoids costly diazo preparations (Platinum Metals Rev. 2005, 49, 33). Also, Furstner et al. have prepared (N,N'-bis(mesityl)imidazol-2-ylidene)$RuCl_2$(3-phenylindenylene). However, these types of complexes have not proven effective in ethenolysis reactions.

In order to obtain an economically viable process for 1-decene production via the cross-metathesis of ethylene and biodiesel (such as animal or vegetable oils), higher activity catalysts must be discovered. Thus, there is a need for higher activity processes that produce desired products and co-products in commercially desirable ratios.

There remains a need for catalysts which demonstrate high activity and selectivity in metathesis cross-reactions, including ethenolysis, which are capable of being synthesized by both mild and affordable synthetic routes. The instant invention's metathesis catalyst compounds provide both a mild and commercially economical and an "atom-economical" route to desirable olefins, in particular alpha-olefins, which in turn may be useful in the preparation of PAOs. More particularly, instant invention's metathesis catalyst compounds demonstrate improved activity and selectivity towards ethenolysis products in ethylene cross-metathesis reactions.

SUMMARY OF THE INVENTION

This invention relates to a metathesis catalyst compound represented by the formula:

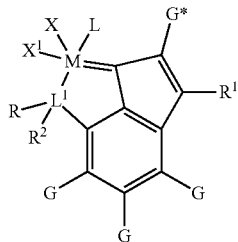

wherein M is a Group 8 metal; X and $X^1$ are anionic ligands; L is a neutral two electron donor; $L^1$ is N or P, preferably N; G* is selected from the group consisting of hydrogen, a $C_1$ to $C_{30}$ hydrocarbyl, and a $C_1$ to $C_{30}$ substituted hydrocarbyl; R is a $C_1$ to $C_{30}$ hydrocarbyl or a $C_1$ to $C_{30}$ substituted hydrocarbyl; $R^1$ is selected from the group consisting of hydrogen, a $C_1$ to $C_{30}$ hydrocarbyl, and a $C_1$ to $C_{30}$ substituted hydrocarbyl; $R^2$ is hydrogen, a $C_1$ to $C_{30}$ hydrocarbyl or a $C_1$ to $C_{30}$ substituted hydrocarbyl; and G is independently selected from the group consisting of hydrogen, halogen, $C_1$ to $C_{30}$ hydrocarbyls, and $C_1$ to $C_{30}$ substituted hydrocarbyls.

This invention also relates to a process to produce alpha olefin (preferably 1-decene) comprising contacting the metathesis catalyst described above with an olefin (preferably ethylene), and one or more triacylglycerides such as fatty acid esters (preferably fatty acid methyl esters, preferably methyl oleate).

In a preferred embodiment, this relates to a process to produce alpha olefin (preferably 1-decene) comprising contacting the metathesis catalyst described above with an olefin (preferably ethylene), and one or more triacylglycerides such as fatty acid esters (preferably fatty acid methyl esters, preferably methyl oleate) derived from biodiesel.

BRIEF DESCRIPTION OF THE FIGURES

FIG. 1 is a representation of the molecular structure of $(PPh_3)Cl_2Ru$(3-pentafluorophenyl-6,8-diisopropoxyinden-1-ylidene) (J) drawn with 30% thermal ellipsoids.

DETAILED DESCRIPTION

The present invention comprises a novel metathesis catalyst compound useful for the cross-metathesis of olefins, and processes for the use thereof More particularly, the present invention comprises a novel metathesis catalyst compound which comprises a chelating indenylene group. Even more particularly, the present invention comprises a novel metathesis catalyst compound which demonstrates improved activity and selectivity towards ethenolysis products in ethylene cross-metathesis reactions.

This invention also relates to a process comprising contacting a feed oil or derivative thereof (and optional alkene) with an olefin metathesis catalyst under conditions which yield an alpha-olefin. Typically, the feed oil is esterified or transesterified with an alcohol prior to contacting with the olefin metathesis catalyst.

This invention also relates to a process comprising contacting a triacylglyceride or a derivative thereof with an optional alkene (such as ethylene) and an olefin metathesis catalyst under conditions which yield an alpha-olefin, typically yielding a linear alpha-olefin (such as 1-decene, 1-heptene, and/or 1-butene) and an ester or acid functionalized olefin.

This invention further relates to a process for producing alpha-olefins (preferably linear alpha-olefins) comprising contacting a triacylglyceride with an alcohol (such as methanol) to produce a fatty acid alkyl ester and thereafter contacting the fatty acid alkyl ester with an olefin metathesis catalyst (and optional alkene, such as ethylene) under conditions which yield an alpha-olefin (preferably a linear alpha-olefin, preferably 1-decene, 1-heptene, and/or 1-butene) and an ester or acid functionalized olefin.

This invention further relates to a process for producing alpha-olefins (preferably linear alpha-olefins) comprising contacting a triacylglyceride with water and/or an alkaline reactant (such as sodium hydroxide) to produce a fatty acid and thereafter contacting the fatty acid with an olefin metathesis catalyst (and optional alkene, such as ethylene) under conditions which yield an alpha-olefin (preferably a linear alpha-olefin, preferably 1-decene, 1-heptene, and/or 1-butene) and an ester or acid functionalized olefin.

This invention further relates to contacting unsaturated fatty acid with an alkene (such as ethylene) in the presence of an olefin metathesis catalyst under conditions which yield an alpha-olefin (preferably a linear alpha-olefin, preferably 1-decene, 1-heptene, and/or 1-butene) and an ester or acid functionalized olefin.

This invention further relates to contacting an unsaturated fatty acid ester with an alkene (such as ethylene) in the presence of an olefin metathesis catalyst under conditions which yield an alpha-olefin (preferably a linear alpha-olefin, preferably 1-decene, 1-heptene, and/or 1-butene) and an ester or acid functionalized olefin.

This invention further relates to contacting an unsaturated fatty acid alkyl ester with an alkene (such as ethylene) in the presence of an olefin metathesis catalyst under conditions which yield an alpha-olefin (preferably a linear alpha-olefin, preferably 1-decene, 1-heptene, and/or 1-butene) and an ester or acid functionalized olefin.

This invention also relates to a process to produce alpha olefin (preferably linear alpha olefin, preferably 1-decene, 1-heptene, and/or 1-butene) comprising contacting a metathesis catalyst with an alkene (preferably ethylene), and one or more fatty acid esters (preferably fatty acid methyl esters, preferably methyl oleate).

In a preferred embodiment, this relates to a process to produce alpha olefin (preferably linear alpha olefin, preferably 1-decene, 1-heptene, and/or 1-butene) comprising contacting a metathesis catalyst with an alkene (preferably ethylene), and one or more fatty acid esters (preferably fatty acid methyl esters, preferably methyl oleate) derived from biodiesel.

In a preferred embodiment, the olefin metathesis catalysts described herein may be combined directly with feed oils, triacylglycerides, biodiesel, fatty acids, fatty acid esters and/or fatty acid alkyl esters to produce alpha-olefins, preferably linear alpha olefins, preferably $C_4$ to $C_{24}$ alpha-olefins, preferably linear alpha-olefins, such as 1-decene, 1-heptene, and/or 1-butene.

In a preferred embodiment, a mixture of one or more biodiesels, triacylglycerides, fatty acids, fatty acid esters and/or fatty acid alkyl esters is used to produce alpha-olefins, preferably linear alpha olefins, preferably $C_4$ to $C_{24}$ alpha-olefins, preferably $C_4$ to $C_{24}$ linear alpha-olefins. In a preferred embodiment a mixture of alpha olefins, preferably linear alpha olefins, preferably 1-decene, 1-heptene, and/or 1-butene is produced.

Process

In a preferred embodiment, the metathesis catalysts described herein may be combined directly with feed oils, seed oils, biodiesel, triacylglycerides, fatty acids, fatty acid esters, and/or fatty acid alkyl esters ("feed materials") to produce alpha-olefins, preferably linear alpha olefins, preferably $C_4$ to $C_{24}$ alpha-olefins, preferably $C_4$ to $C_{24}$ linear alpha-olefins, such as preferably 1-decene, 1-heptene, and/or 1-butene.

Typically, the molar ratio of alkene to unsaturated feed material (such as unsaturated fatty acid or fatty acid ester) is greater than about 0.8/1.0, preferably greater than about 0.9/1.0. Typically, the molar ratio of alkene to feed material (such as unsaturated fatty acid or fatty acid ester) is less than about 3.0/1.0, preferably less than about 2.0/1.0. Depending upon the specific reagents, other molar ratios may also be suitable. With ethylene, for example, a significantly higher molar ratio can be used, because the self-metathesis of ethylene produces only ethylene again; no undesirable co-product olefins are formed. Accordingly, the molar ratio of ethylene to feed material (such as unsaturated fatty acid or fatty acid ester) may range from greater than about 0.8/1 to typically less than about 20/1.

The quantity of metathesis catalyst that is employed in the process of this invention is any quantity that provides for an operable metathesis reaction. Preferably, the ratio of moles of feed material (preferably fatty acid ester and/or fatty acid alkyl ester) to moles of metathesis catalyst is typically greater than about 10:1, preferably greater than about 100:1, preferably greater than about 1000:1, preferably greater than about 10,000:1, preferably greater than about 25,000:1, preferably greater than about 50,000:1, preferably greater than about 100,000:1. Alternately, the molar ratio of feed material (preferably fatty acid ester and/or fatty acid alkyl ester) to metathesis catalyst is typically less than about 10,000,000:1, preferably less than about 1,000,000:1, and more preferably less than about 500,000:1.

The contacting time of the reagents and catalyst in a batch reactor can be any duration, provided that the desired olefin metathesis products are obtained. Generally, the contacting time in a reactor is greater than about 5 minutes, and preferably greater than about 10 minutes. Generally, the contacting time in a reactor is less than about 25 hours, preferably less than about 15 hours, and more preferably less than about 10 hours.

In a preferred embodiment, the reactants (for example, metathesis catalyst; feed materials; optional alkene, optional alcohol, optional water, etc.) are combined in a reaction vessel at a temperature of 20 to 300° C. (preferably 20 to 200° C., preferably 30 to 100° C., preferably 40 to 60° C.) and an alkene (such as ethylene) at a pressure of 0.1 to 1000 psi (0.7 kPa to 6.9 MPa) (preferably 20 to 400 psi (0.14 MPa to 2.8 MPa), preferably 50 to 250 psi (0.34 MPa to 1.7 MPa)), if the alkene is present, for a residence time of 0.5 seconds to 48 hours (preferably 0.25 to 5 hours, preferably 30 minutes to 2 hours).

In certain embodiments, where the alkene is a gaseous olefin, the olefin pressure is greater than about 5 psig (34.5 kPa), preferably greater than about 10 psig (68.9 kPa), and more preferably greater than about 45 psig (310 kPa). When a diluent is used with the gaseous alkene, the aforementioned pressure ranges may also be suitably employed as the total pressure of olefin and diluent. Likewise, when a liquid alkene is employed and the process is conducted under an inert gaseous atmosphere, then the aforementioned pressure ranges may be suitably employed for the inert gas pressure.

In a preferred embodiment, from about 0.005 nmoles to about 500 nmoles, preferably from about 0.1 to about 250 nmoles, and most preferably from about 1 to about 50 nmoles of the metathesis catalyst are charged to the reactor per 3 mmoles of feed material (such as triacylglycerides, biodiesel, fatty acids, fatty acid esters, and/or fatty acid alkyl esters or mixtures thereof, preferably fatty acid esters) charged.

In a preferred embodiment, the alkene and an unsaturated fatty acid ester or unsaturated fatty acid are co-metathesized to form first and second product olefins, preferably a reduced chain first product alpha-olefin and a second product reduced chain terminal ester or acid-functionalized alpha-olefin. As a preferred example, the metathesis of methyloleate with ethylene will yield co-metathesis products of 1-decene and methyl-9-decenoate. Both products are alpha-olefins; the decenoate also terminates in an ester moiety at the opposite end of the chain from the carbon-carbon double bond. In addition to the desired products, the methyloleate may self-metathesize to produce small amounts of 9-octadecene, a less desirable product, and dimethyl-9-octadecene-1,18-dioate, $CH_3OC(O)(CH_2)_7CH{=}CH(CH_2)_7C(O)OCH_3$, a second less desirable product.

In the process of this invention, the conversion of feed material (preferably fatty acid ester and/or fatty acid alkyl ester) can vary widely depending upon the specific reagent olefins, the specific catalyst, and specific process conditions employed. For the purpose of this invention, "conversion" is defined as the mole percentage of feed material that is converted or reacted to the cross-metathesis alpha-olefin products. Typically, the conversion of feed material (preferably fatty acid ester and/or fatty acid alkyl ester) is greater than about 50 mole percent, preferably greater than about 60 mole percent, and more preferably greater than about 70 mole percent.

In the process of this invention, the yields of first product olefin and ester or acid-functionalized second product olefin can also vary depending upon the specific reagent olefins, catalyst, and process conditions employed. For the purposes of this invention "yield" will be defined as the mole percentage of cross-metathesis alpha-olefin product olefin formed relative to the initial moles of feed material (such as fatty acid ester and/or fatty acid alkyl ester) in the feed. Typically, the yield of alpha-olefin will be greater than about 35 mole percent, preferably greater than about 50 mole percent. Typically, the yield of ester or acid-functionalized alpha-olefin will be greater than about 35 mole percent, preferably greater than about 50 mole percent.

In a preferred embodiment, the process is typically a solution process, although it may be a bulk or high pressure process. Homogeneous processes are preferred. (A homogeneous process is defined to be a process where at least 90 wt % of the product is soluble in the reaction media.) A bulk homogeneous process is particularly preferred. (A bulk process is defined to be a process where reactant concentration in all feeds to the reactor is 70 volume % or more.) Alternately no solvent or diluent is present or added in the reaction medium, (except for the small amounts used as the carrier for the catalyst or other additives, or amounts typically found with the reactants; e.g., propane in propylene).

Suitable diluents/solvents for the process include non-coordinating, inert liquids. Examples include straight and branched-chain hydrocarbons such as isobutane, butane, pentane, isopentane, hexanes, isohexane, heptane, octane, dodecane, and mixtures thereof; cyclic and alicyclic hydrocarbons such as cyclohexane, cycloheptane, methylcyclohexane, methylcycloheptane, and mixtures thereof such as can be found commercially (Isopar™); perhalogenated hydrocarbons such as perfluorinated $C_{4-10}$ alkanes, chlorobenzene, and aromatic and alkylsubstituted aromatic compounds such as benzene, toluene, mesitylene, and xylene. Suitable diluents/solvents also include aromatic hydrocarbons, such as toluene or xylenes, and chlorinated solvents, such as dichloromethane. In a preferred embodiment, the feed concentration for the process is 60 volume % solvent or less, preferably 40 volume % or less, preferably 20 volume % or less.

The process may be batch, semi-batch, or continuous. As used herein, the term continuous means a system that operates without interruption or cessation. For example, a continuous process to produce a metathesis product would be one where the reactants are continually introduced into one or more reactors and cross-metathesis alpha-olefin product is continually withdrawn.

Useful reaction vessels include reactors (including continuous stirred tank reactors, batch reactors, reactive extruder, pipe, or pump).

The processes may be conducted in either glass lined, stainless steel, or similar type reaction equipment. Useful reaction vessels include reactors (including continuous stirred tank reactors, batch reactors, reactive extruder, pipe or pump, continuous flow fixed bed reactors, slurry reactors, fluidized bed reactors, and catalytic distillation reactors). The reaction zone may be fitted with one or more internal and/or external heat exchanger(s) in order to control undue temperature fluctuations, or to prevent "runaway" reaction temperatures.

If the process is conducted in a continuous flow reactor, then the weight hourly space velocity, given in units of grams feed material (preferably fatty acid ester and/or fatty acid alkyl ester) per gram catalyst per hour ($h^{-1}$), will determine the relative quantities of feed material to catalyst employed, as well as the residence time in the reactor of the unsaturated starting compound. In a flow reactor, the weight hourly space velocity of the unsaturated feed material (preferably fatty acid ester and/or fatty acid alkyl ester) is typically greater than about 0.04 g feed material (preferably fatty acid ester and/or fatty acid alkyl ester) per g catalyst per hour ($h^{-1}$), and preferably greater than about 0.1 $h^{-1}$. In a flow reactor, the weight hourly space velocity of the feed material (preferably fatty acid ester and/or fatty acid alkyl ester) is typically less than about 100 $h^{-1}$, and preferably less than about 20 $h^{-1}$.

In certain embodiments, reactions utilizing the catalytic complexes of the present invention can be run in a biphasic mixture of solvents, in an emulsion or suspension, or in a lipid vesicle or bilayer.

The feed material is typically provided as a liquid phase, preferably neat. In particular embodiments, the feed material is provided in a liquid phase, preferably neat; while the alkene is provided as a gas that is dissolved in the liquid phase. In certain embodiments, feed material is an unsaturated fatty acid ester or unsaturated fatty acid and is provided in a liquid phase, preferably neat; while the alkene is a gaseous alpha-olefin, such as for example, ethylene, which is dissolved in the liquid phase.

Generally, the feed material is an unsaturated fatty acid ester or unsaturated fatty acid and is provided as a liquid at the process temperature, and it is generally preferred to be used neat, that is, without a diluent or solvent. The use of a solvent usually increases recycle requirements and increases costs. Optionally, however, if desired, a solvent can be employed with the alkene and/or feed material. A solvent may be desirable, for instance, where liquid feed material and alkene are not entirely miscible, and both then can be solubilized in a suitable solvent.

In a preferred embodiment, the productivity of the process is at least 200 g of linear alpha-olefin (such as decene-1) per mmol of catalyst per hour, preferably at least 5000 g/mmol/hour, preferably at least 10,000 g/mmol/hr, preferably at least 300,000 g/mmol/hr. For the purposes of this invention, "productivity" is defined to be the amount in grams of linear alpha-olefin produced per mmol of catalyst introduced into the reactor, per hour.

For the purposes of this invention, selectivity is a measure of conversion of alkene and feed material to the cross-metathesis alpha-olefin product, and is defined by the mole percentage of product olefin formed relative to the initial moles of alkene or feed material. In a preferred embodiment, the selectivity of the process is at least 20 wt % linear alpha-olefin, based upon the weight to the material exiting the reactor, preferably at least 25%, preferably at least 30%, preferably at least 35%.

For the purpose of this invention, catalyst turnover number (TON) is a measure of how active the catalyst compound is and is defined as the number of moles of cross-metathesis alpha-olefin product formed per mole of catalyst compound. In a preferred embodiment, the (TON), of the process is at least 10,000, preferably at least 50,000, preferably at least 100,000, preferably at least 1,000,000.

In a preferred embodiment, the alpha olefin yield (when converting unsaturated fatty acids, unsaturated fatty acid esters, unsaturated fatty acid alkyl esters, or mixtures thereof), defined as the mole percentage of cross metathesis alpha olefin product formed per mole of unsaturated fatty acids, unsaturated fatty acid esters, unsaturated fatty acid alkyl esters, or mixtures thereof introduced into the reactor, is 30% or more, preferably 40% or more, preferably 45% or more, preferably 50% or more, preferably 55% or more, preferably 60% or more.

In a preferred embodiment, the yield for reactions (when converting triacylglycerides as represented in the formula below), is defined as the moles of alpha olefin formed divided by (the moles of unsaturated $R^a$+moles of unsaturated $R^b$+moles of unsaturated $R^c$) introduced into the reactor is 30% or more, preferably 40% or more, preferably 45% or more, preferably 50% or more, preferably 55% or more, preferably 60% or more,

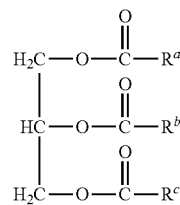

where $R^a$, $R^b$, and $R^c$ each, independently, represent a saturated or unsaturated hydrocarbon chain (preferably $R^a$, $R^b$, and $R^c$ each, independently, are a $C_{12}$ to $C_{28}$ alkyl or alkene, preferably $C_{16}$ to $C_{22}$ alkyl or alkene).

Alkenes

Besides the feed materials, the metathesis process of this invention may use an alkene as a reactant. The term "alkene" shall mean an organic compound containing at least one carbon-carbon double bond. Alkenes useful herein typically have less than about 10 carbon atoms. The alkene may have one carbon-carbon unsaturated bond, or alternatively, two or more carbon-carbon unsaturated bonds. Since the metathesis reaction can occur at any double bond, alkenes having more than one double bond will produce more metathesis products.

Accordingly, in some embodiments, it is preferred to employ an alkene having only one carbon-carbon double bond. The double bond may be, without limitation, a terminal double bond or an internal double bond. The alkene may also be substituted at any position along the carbon chain with one or more substituents, provided that the one or more substituents are essentially inert with respect to the metathesis process. Suitable substituents include, without limitation, alkyl, preferably $C_{1-6}$ alkyl; cycloalkyl, preferably $C_{3-6}$ cycloalkyl; as well as hydroxy, ether, keto, aldehyde, and halogen functionalities. Non-limiting examples of suitable alkenes include ethylene, propylene, butene, butadiene, pentene, hexene, the various isomers thereof, as well as higher homologues thereof. Preferably, the alkene is a $C_{2-8}$ alkene. More preferably the alkene is a $C_{2-6}$ alkene, even more preferably a $C_{2-4}$ alkene, and most preferably ethylene.

Useful alkenes include those represented by the formula: $R^*$—HC=CH—$R^*$, wherein each $R^*$ is independently, hydrogen or a $C_1$ to $C_{20}$ hydrocarbyl, preferably hydrogen or a $C_1$ to $C_6$ hydrocarbyl, preferably hydrogen, methyl, ethyl, propyl or butyl, more preferably $R^*$ is hydrogen. In a preferred embodiment, both $R^*$ are the same, preferably both $R^*$ are hydrogen. Ethylene, propylene, butene, pentene, hexene, octene, and nonene (preferably ethylene) are alkenes useful herein.

For purposes of this invention and the claims thereto, the term lower olefin means an alkene represented by the formula: $R^*$—HC=CH—$R^*$, wherein each $R^*$ is independently, hydrogen or a $C_1$ to $C_6$ hydrocarbyl, preferably hydrogen or a $C_1$ to $C_3$ hydrocarbyl, preferably hydrogen, methyl, ethyl, propyl or butyl, more preferably $R^*$ is hydrogen. In a preferred embodiment, both $R^*$ are the same, preferably both $R^*$ are hydrogen. Ethylene, propylene, butene, pentene, hexene, and octene (preferably ethylene) are lower olefins useful herein.

Triacylglycerides

Triacylglycerides (TAGs), also called triglycerides, are a naturally occurring ester of three fatty acids and glycerol that is the chief constituent of natural fats and oils. The three fatty acids can be all different, all the same, or only two the same, they can be saturated or unsaturated fatty acids, and the saturated fatty acids may have one or multiple unsaturations. Chain lengths of the fatty acids in naturally occurring triacylglycerides can be of varying lengths, but 16, 18, and 20 carbons are the most common Natural fatty acids found in plants and animals are typically composed only of even numbers of carbon atoms due to the way they are bio-synthesized. Most natural fats contain a complex mixture of individual triglycerides and because of this, they melt over a broad range of temperatures.

Biodiesel is a mono-alkyl ester derived from the processing of vegetable or animal oils and alcohols. The processing is typically carried out by an esterification reaction mechanism, and typically is performed in an excess of alcohol to maximize conversion. Esterification can refer to direct esterification, such as between a free fatty acid and an alcohol, as well as transesterification, such as between an ester and an alcohol. While vegetable oil and alcohols are commonly employed as reactants in esterification reactions, a fatty acid source such as free fatty acids, soaps, esters, glycerides (mono-, di-, tri-), phospholipids, lysophospholipids, or amides and a monohydric alcohol source, such as an alcohol or an ester, can be esterified. In addition, various combinations of these reagents can be employed in an esterification reaction.

Vegetable and animal oils include triglycerides and neutral fats, such as triacylglyderides, the main energy storage form of fat in animals and plants. These typically have the chemical structure:

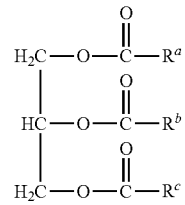

where $R^a$, $R^b$, and $R^c$ each, independently, represent a saturated or non-saturated hydrocarbon chain (preferably $R^a$, $R^b$, and $R^c$ each, independently, are a $C_{12}$ to $C_{28}$ alkyl or alkene, preferably $C_{16}$ to $C_{22}$ alkyl or alkene). Different vegetable oils have different fatty acid profiles, with the same or different fatty acids occurring on a single glycerol. For example, an oil can have linoleic, oleic, and stearic acids attached to the same glycerol, with each of $R^a$, $R^b$, and $R^c$ representing one of these three fatty acids. In another example, there can be two oleic acids and one stearic acid attached to the same glycerol, each of $R^a$, $R^b$, and $R^c$ representing one of these fatty acids. A particularly useful triglyceride consists of three fatty acids (e.g., saturated fatty acids of general structure of $CH_3(CH_2)_n$ COOH, wherein n is typically an integer of from 4 to 28 or higher) attached to a glycerol $(C_3H_5(OH)_3)$ backbone by ester linkages. In the esterification process, vegetable oils and short chain alcohols are reacted to form mono-alkyl esters of the fatty acid and glycerol (also referred to as glycerin). When the alcohol used is methanol ($CH_3OH$), a methyl ester is created with the general form $CH_3(CH_2)_nCOOCH_3$ for saturated fatty acids. Typically, but not always, the length of the carbon backbone chain is from 12 to 24 carbon atoms.

The esterification process can be catalyzed or non-catalyzed. Catalyzed processes are categorized into chemical and enzyme based processes. Chemical catalytic methods can employ acid and/or base catalyst mechanisms. The catalysts can be homogeneous and/or heterogeneous catalysts. Homogeneous catalysts are typically liquid phase mixtures, whereas heterogeneous catalysts are solid phase catalysts mixed with the liquid phase reactants, oils and alcohols.

The fatty acid rich material useful in the processes described herein can be derived from plant, animal, microbial, or other sources (feed oil). Preferred feed oils include vegetable oils such as corn, soy, rapeseed, canola, sunflower, palm, and other oils that are readily available; however, any vegetable oil or animal fat can be employed. Raw or unrefined oil can be used in certain embodiments; however, filtered and refined oils are typically preferred. Use of degummed and filtered feedstock minimizes the potential for emulsification and blockage in the reactors. Feedstock with high water content can be dried before basic catalyst processing. Feedstock with high free fatty acid content can be passed through an esterification process to reduce the free fatty acid content before the process of esterification to convert fatty acid glycerides to monoalkyl esters. The reduction of free fatty acids and the conversion of fatty acid glycerides can also be in the same processing step. Feedstock containing other organic compounds (such as hexane, heptane, isohexane, etc.) can typically be processed without significant modifications to the reactor. Other materials containing fatty acid glycerides or other fatty acid esters can also be employed, including phospholipids, lysophospholipids, and fatty acid wax esters. The fatty acid rich material useful in the processes described herein typically includes a mixture of fatty acids. For example, the fatty acid profiles of several useful feedstocks are shown in Table 1. The feed oil used as feedstock can also include a mixture of fatty acid glycerides from different sources. The free fatty acid content of useful vegetable oils is preferably about 0.1 wt % or less when employed in a basic homogeneous catalyst esterification reaction. Higher levels can be utilized as well, and levels up to about 3 wt %, or even as high as 15 wt % or more can typically be tolerated.

TABLE 1

Fatty Acid Profile of Several Typical Feed Oils

| Fatty Acid | Palm Oil | Soy Oil | High Oleic (a.k.a. Hi Oleic) Rapeseed | Yellow Grease |
| --- | --- | --- | --- | --- |
|  | 0 wt % | 0 wt % | 0 wt % | 0 wt % |
| C6:0 | 0 wt % | 0 wt % | 0 wt % | 0 wt % |
| C8:0 | 0 wt % | 0 wt % | 0 wt % | 0 wt % |
| C10:0 | 0 wt % | 0 wt % | 0 wt % | 0 wt % |
| C12:0 | 0 wt % | 0 wt % | 0 wt % | 0 wt % |
| C14:0 | 1 wt % | 0 wt % | 0 wt % | 2 wt % |
| C16:0 | 44 wt % | 7 wt % | 4 wt % | 23 wt % |
| C18:0 | 5 wt % | 5 wt % | 1 wt % | 13 wt % |
| C18:1 | 39 wt % | 28 wt % | 60 wt % | 44 wt % |
| C18:2 | 10 wt % | 53 wt % | 21 wt % | 7 wt % |
| C18:3 | 0 wt % | 0 wt % | 13 wt % | 1 wt % |
| C20:0 | 0 wt % | 0 wt % | 0 wt % | 0 wt % |
| C22:1 | 0 wt % | 0 wt % | 0 wt % | 0 wt % |
| Misc. | 1 wt % | 8 wt % | 0 wt % | 9 wt % |
| Total | 100 wt % | 100 wt % | 100 wt % | 100 wt % |

Alcohol (Also Referred to as Alkanols)

The alcohol used herein can be any monohydric, dihydric, or polyhydric alcohol that is capable of condensing with the feed material (such as the unsaturated fatty acid) to form the corresponding unsaturated ester (such as the fatty acid ester). Typically, the alcohol contains at least one carbon atom. Typically, the alcohol contains less than about 20 carbon atoms, preferably less than about 12 carbon atoms, and more preferably less than about 8 carbon atoms. The carbon atoms may be arranged in a straight-chain or branched structure, and may be substituted with a variety of substituents, such as those previously disclosed hereinabove in connection with the fatty acid, including the aforementioned alkyl, cycloalkyl, monocyclic aromatic, arylalkyl, alkylaryl, hydroxyl, halogen, ether, ester, aldehyde and keto substituents. Preferably, the alcohol is a straight-chain or branched $C_{1-12}$ alkanol. A preferred alcohol is the trihydric alcohol glycerol, the fatty acid esters of which are known as "glycerides." Other preferred alcohols include methanol and ethanol.

Preferably, the alcohol employed in the esterification and/or transesterification reactions is preferably a low molecular weight monohydric alcohol such as methanol, ethanol, 1-propanol, 2-propanol, 1-butanol, 2-butanol, or t-butanol. The alcohol is preferably anhydrous; however, a small amount of water in the alcohol may be present (e.g., less than about 2 wt %, preferably less than about 1 wt %, and most preferably less than about 0.5 wt %; however, in certain embodiments higher amounts can be tolerated). Acid esterification reactions are more tolerant of the presence of small amounts of water in the alcohol than are basic transesterification reactions. While specific monohydric alcohols are discussed herein with reference to certain embodiments and examples, the preferred embodiments are not limited to such specific monohydric alcohols. Other suitable monohydric alcohols can also be employed in the preferred embodiments.

Transesterification/Esterification Reactions

The conversion of TAGs to fatty acid alkyl esters ("FAAE") through transesterification of the TAG typically involves forming a reactant stream, which includes TAG (e.g., at least about 75 wt %), alkanol (e.g., about 5 wt % to 20 wt %), a transesterification catalyst (e.g., about 0.05 wt % to 1 wt %), and optionally, glycerol (typically up to about 10 wt %). Suitable alkanols may include $C_1$ to $C_6$ alkanols and commonly may include methanol, ethanol, or mixtures thereof. Suitable transesterification catalysts may include alkali metal alkoxides having from 1 to 6 carbon atoms and commonly may include alkali metal methoxide, such as sodium methoxide and/or potassium methoxide. The basic catalyst is desirably selected such that the alkali metal alkoxide may suitably contain an alkoxide group which is the counterpart of the alkanol employed in the reaction stream (e.g., a combination of methanol and an alkali metal methoxide such as sodium methoxide and/or potassium methoxide). The reactant stream may suitably include about 0.05 wt % to 0.3 wt % sodium methoxide, at least about 75 wt % triacylglyceride, about 1 wt % to 7 wt % glycerol, and at least about 10 wt % methanol. In some embodiments, the reactant stream may desirably include about 0.05 wt % to 0.25 wt % sodium methoxide, at least about 75 wt % triacylglyceride, about 2 wt % to 5 wt % glycerol, and about 10 wt % to 15 wt % methanol.

The rate and extent of reaction for esterification of the fatty acid glycerides or other fatty acid derivates with monohydric alcohol in the presence of a catalyst depends upon factors including, but not limited to, the concentration of the reagents, the concentration and type of catalyst, the temperature and pressure conditions, and time of reaction. The reaction generally proceeds at temperatures above about 50° C., preferably at temperatures above 65° C.; however, the catalyst selected or the amount of catalyst employed can affect this temperature to some extent. Higher temperatures generally result in faster reaction rates. However, the use of very high temperatures, such as those in excess of about 300° C., or even those in excess of 250° C., can lead to increased generation of side products, which can be undesirable as their presence can increase downstream purification costs. Higher temperatures can be advantageously employed, however, e.g., in situations where the side products do not present an issue.

The reaction temperature can be achieved by preheating one or more of the feed materials or by heating a mixture of the feed materials. Heating can be achieved using apparatus known in the art, e.g., heat exchangers, jacketed vessels, submerged coils, and the like. While specific temperatures and methods of obtaining the specific temperatures are discussed herein with reference to certain embodiments and examples, the preferred embodiments are not limited to such specific temperatures and methods of obtaining the specific temperatures. Other temperatures and methods of obtaining temperatures can also be employed in the preferred embodiments.

The amount of alcohol employed in the reaction is preferably in excess of the amount of fatty acid present on a molar basis. The fatty acid can be free or combined, such as to alcohol, glycol or glycerol, with up to three fatty acid moieties being attached to a glycerol. Additional amounts of alcohol above stoichiometric provide the advantage of assisting in driving the equilibrium of the reaction to produce more of the fatty acid ester product. However, greater excesses of alcohol can result in greater processing costs and larger capital investment for the larger volumes of reagents employed in the process, as well as greater energy costs associated with recovering, purifying, and recycling this excess alcohol. Accordingly, it is generally preferred to employ an amount of alcohol yielding a molar ratio of alcohol to fatty acid of from about 15:1 to about 1:1 (stoichiometric), and more preferably from about 4:1 to about 2:1; however, the process can operate over a much wider range of alcohol to fatty acid ratios, with non-reacted materials subjected to recycling or other processing steps. Generally, lower relative levels of alcohol to fatty acid result in decreased yield and higher relative levels of alcohol levels to fatty acid result in increased capital and operating expense. Some instances of operation at ratios of alcohol to fatty acid over a wider range include when first starting up the process or shutting down the process, when balancing the throughput of the reactor to other processing steps or other processing facilities, such as one that produces alcohol or utilizes a side stream, or when process upsets occur. When a molar ratio of 2:1 methanol to fatty acid is employed and a sodium hydroxide concentration of about 0.5 wt % of the total reaction mixture is employed, the ratio of sodium hydroxide to methanol is about 2 wt % entering the reactor and about 4 wt % at the exit because about half of the alcohol is consumed in the esterification reaction.

Similarly, higher amounts of catalyst generally result in faster reactions. However, higher amounts of catalyst can lead to higher downstream separation costs and a different profile of side reaction products. The amount of homogeneous catalyst is preferably from about 0.2 wt % to about 1.0 wt % of the reaction mixture when the catalyst is sodium hydroxide; at typical concentration of 0.5 wt % when a 2:1 molar ratio of methanol to fatty acid is used; however, in certain embodiments higher or lower amounts can be employed. The amount of catalyst employed can also vary depending upon the nature of the catalyst, feed materials, operating conditions, and other factors. Specifically, the temperature, pressure, free fatty acid content of the feed, and degree of mixing can change the amount of catalyst preferably employed. While specific catalyst amounts are discussed herein with reference to certain embodiments and examples, the preferred embodiments are not limited to such specific catalyst amounts. Other suitable catalyst amounts can also be employed in the preferred embodiments.

The esterification reaction can be performed batchwise, such as in a stirred tank, or it can be performed continuously, such as in a continuous stirred tank reactor (CSTR) or a plug flow reactor (PFR). When operated in continuous mode, a series of continuous reactors (including CSTRs, PFRs, or combinations thereof) can advantageously operate in series. Alternatively, batch reactors can be arranged in parallel and/or series.

When the reactor is operated in a continuous fashion, one or more of the feed materials is preferably metered into the process. Various techniques for metering can be employed (e.g., metering pumps, positive displacement pumps, control valves, flow meters, and the like). While specific types of reactors are discussed herein with reference to certain embodiments and examples, the preferred embodiments are not limited to such specific reactors. Other suitable types of reactors can also be employed in the preferred embodiments.

Fatty Acids and Fatty Acid Esters

Fatty acids are carboxylic acids with a saturated or unsaturated aliphatic tails that are found naturally in many different fats and oils. Any unsaturated fatty acid can be suitably employed in the process of this invention, provided that the unsaturated fatty acid can be metathesized in the manner disclosed herein. An unsaturated fatty acid comprises a long carbon chain containing at least one carbon-carbon double bond and terminating in a carboxylic acid group. Typically, the unsaturated fatty acid will contain greater than about 8 carbon atoms, preferably greater than about 10 carbon atoms, and more preferably greater than about 12 carbon atoms. Typically, the unsaturated fatty acid will contain less than about 50 carbon atoms, preferably less than about 35 carbon atoms, and more preferably less than about 25 carbon atoms. At least one carbon-carbon double bond is present along the carbon chain, this double bond usually occurring about the middle of the chain, but not necessarily. The carbon-carbon double bond may also occur at any other internal location along the chain. A terminal carbon-carbon double bond, at the opposite end of the carbon chain relative to the terminal carboxylic acid group, is also suitably employed, although terminal carbon-carbon double bonds occur less commonly in fatty acids. Unsaturated fatty acids containing the terminal carboxylic acid functionality and two or more carbon-carbon double bonds may also be suitably employed in the process of this invention. Since metathesis can occur at any of the carbon-carbon double bonds, a fatty acid having more than one double bond may produce a variety of metathesis products. The unsaturated fatty acid may be straight or branched and substituted along the fatty acid chain with one or more substituents, provided that the one or more substituents are substantially inert with respect to the metathesis process. Non-limiting examples of suitable substituents include alkyl moieties, preferably $C_{1-10}$ alkyl moieties, including, for example, methyl, ethyl, propyl, butyl, and the like; cycloalkyl moieties, preferably $C_{4-8}$ cycloalkyl moieties, including for example, cyclopentyl and cyclohexyl; monocyclic aromatic moieties, preferably $C_6$ aromatic moieties, that is, phenyl; arylalkyl moieties, preferably $C_{7-16}$ arylalkyl moieties, including, for example, benzyl; and alkylaryl moieties, preferably $C_{7-16}$ alkylaryl moieties, including, for example, tolyl, ethylphenyl, xylyl, and the like; as well as hydroxyl, ether, keto, aldehyde, and halide, preferably chloro and bromo, functionalities.

Non-limiting examples of suitable unsaturated fatty acids include 3-hexenoic (hydrosorbic), trans-2-heptenoic, 2-octenoic, 2-nonenoic, cis- and trans-4-decenoic, 9-decenoic (caproleic), 10-undecenoic (undecylenic), trans-3-dodecenoic (linderic), tridecenoic, cis-9-tetradeceonic (myristoleic), pentadecenoic, cis-9-hexadecenoic (cis-9-palmitoelic), trans-9-hexadecenoic (trans-9-palmitoleic), 9-heptadecenoic, cis-6-octadecenoic (petroselinic), trans-6-octadecenoic (petroselaidic), cis-9-octadecenoic (oleic), trans-9-octadecenoic (elaidic), cis-11-octadecenoic, trans-11-octadecenoic (vaccenic), cis-5-eicosenoic, cis-9-eicosenoic (gadoleic), cis-11-docosenoic (cetoleic), cis-13-docosenoic (erucic), trans-13-docosenoic (brassidic), cis-15-tetracosenoic (selacholeic), cis-17-hexacosenoic (ximenic), and cis-21-triacontenoic (lumequeic) acids, as well as 2,4-hexadienoic (sorbic), cis-9-cis-12-octadecadienoic (linoleic), cis-9-cis-12-cis-15-octadecatrienoic (linolenic), eleostearic, 12-hydroxy-cis-9-octadecenoic (ricinoleic), and like acids. Oleic acid is most preferred. Unsaturated fatty acids can be obtained commercially or synthesized by saponifying fatty acid esters, this method being known to those in the art.

Fatty acid esters are formed by condensation of a fatty acid and an alcohol. Fatty acid alkyl esters are fatty acids where the hydrogen of the —OH of the acid group is replaced by a hydrocarbyl group, typically a $C_1$ to $C_{30}$ alkyl group, preferably a $C_1$ to $C_{20}$ alkyl.

Fatty acid alkyl esters are fatty acids where the hydrogen of the —OH of the acid group is replaced by an alkyl group. Fatty acid alkyl esters useful herein are typically represented by the formula: Rˆ—C(O)—O—R*, where Rˆ is a $C_1$ to $C_{100}$ hydrocarbyl group, preferably a $C_6$ to $C_{22}$ group, preferably a $C_6$ to $C_{14}$ 1-alkene group, and R* is an alkyl group, preferably a $C_1$ to $C_{20}$ alkyl group, preferably methyl, ethyl, butyl, pentyl, and hexyl. Preferred fatty acid alkyl esters useful herein are typically represented by the formula: $R\hat{}$—$CH_2$=$CH_2$—$R\hat{}$—$C(O)$—$O$—$R*$, where each $R\hat{}$ is, independently a $C_1$ to $C_{100}$ alkyl group, preferably a $C_6$ to $C_{20}$, preferably a $C_8$ to $C_{14}$ alkyl group, preferably a $C_9$ group and $R*$ is an alkyl group, preferably a $C_1$ to $C_{20}$ alkyl group, preferably methyl, ethyl, butyl, pentyl, and hexyl. Particularly preferred fatty acid alkyl esters useful herein are represented by the formula:

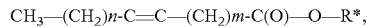

where and $R*$ is an alkyl group, preferably a $C_1$ to $C_{20}$ alkyl group, preferably methyl, ethyl, butyl, pentyl, and hexyl, m and n are, independently 1, 2, 3, 4, 5, 6, 7, 8, 9, 10, 11, 12, 13, 14, 15, or 16, preferably 5, 7, 9, or 11, preferably 7.

Fatty acid methyl esters are fatty acids where the hydrogen of the —OH of the acid group is replaced by methyl group. Fatty acid methyl esters useful herein are typically represented by the formula: $R\hat{}$—$C(O)$—$O$—$CH_3$, where $R\hat{}$ is a $C_1$ to $C_{100}$ hydrocarbyl group, preferably a $C_6$ to $C_{22}$ group, preferably a $C_6$ to $C_{14}$ 1-alkene group. Preferred fatty acid methyl esters useful herein are typically represented by the formula: $R\hat{}$—$CH_2$=$CH_2$—$R\hat{}$—$C(O)$—$O$—$CH_3$, where each $R\hat{}$ is, independently a $C_1$ to $C_{100}$ alkyl group, preferably a $C_6$ to $C_{20}$, preferably a $C_8$ to $C_{14}$ alkyl group, preferably a $C_9$ group. Particularly preferred fatty acid methyl esters useful herein are represented by the formula: $CH_3$—$(CH_2)n$—$C$=$C$—$(CH_2)m$-$C(O)$—$O$—$CH_3$, where m and n are, independently 1, 2, 3, 4, 5, 6, 7, 8, 9, 10, 11, 12, 13, 14, 15, or 16, preferably 5, 7, 9, or 11, preferably 7.

Preferred fatty acid methyl esters include methyl palmitoleate, methyl oleate, methyl gadoleate, methyl erucate, methyl linoleate, methyl linolenate, methyl soyate, and mixtures of methyl esters derived from soybean oil, beef tallow, tall oil, animal fats, waste oils/greases, rapeseed oil, algae oil, canola oil, palm oil, Jathropa oil, high-oleic soybean oil (e.g., 75 mole % or more, preferably 85 mole % or more, preferably 90 mole % or more), high-oleic safflower oil (e.g., 75 mole % or more, preferably 85 mole % or more, preferably 90 mole % or more), high-oleic sunflower oil (e.g., 75 mole % or more, preferably 85 mole % or more, preferably 90 mole % or more), and other plant or animal derived sources containing fatty acids.

A preferred source of fatty acid methyl esters for use herein includes TAG's and biodiesel sources. As described above, biodiesel refers to a transesterified vegetable oil or animal fat based diesel fuel containing long-chain alkyl (typically methyl, propyl, or ethyl) esters. Biodiesel is typically made by chemically reacting lipids (such as vegetable oil) with an alcohol. Biodiesel, TAG's and derivatives thereof may be used in the processes described herein. Likewise, preferred fatty acid methyl esters useful herein may be obtained by reacting canola oil, corn oil, soybean oil, beef tallow, tall oil, animal fats, waste oils/greases, rapeseed oil, algae oil, canola oil, palm oil, Jathropa oil, high-oleic soybean oil, high-oleic safflower oil, high-oleic sunflower oil, or mixtures of animal and/or vegetable fats and oils with one or more alcohols (as described above), preferably methanol.

Vegetable oils useful herein preferably contain at least one site of unsaturation and include, but are not limited to, canola, soybean, palm, peanut, mustard, sunflower, tung, tall, perilla, grapeseed, rapeseed, linseed, safflower, pumpkin, corn, and other oils extracted from plant seeds.

For purposes of this invention and the claims thereto the term "feed oil" refers to one or more plant, animal or microbial oils, including, but not limited to, canola oil, corn oil, soybean oil, fish oil, beef tallow, tall oil, animal fats, waste oils/greases, rapeseed oil, algae oil, peanut oil, mustard oil, sunflower oil, tung oil, perilla oil, grapeseed oil, linseed oil, safflower oil, pumpkin oil, palm oil, Jathropa oil, high-oleic soybean oil, high-oleic safflower oil, high-oleic sunflower oil, mixtures of animal and/or vegetable fats and oils, castor bean oil, dehydrated castor bean oil, cucumber oil, poppyseed oil, flaxseed oil, lesquerella oil, walnut oil, cottonseed oil, meadowfoam, tuna oil, and sesame oils.

In a preferred embodiment, a combination of oils is used herein. Preferred combinations include two (three or four) or more of tall oil, palm oil, tallow, waste grease, rapeseed oil, canola oil, soy oil, and algae oil. Alternate useful combinations include two (three or four) or more of soy oil, canola oil, rapeseed oil, algae oil, and tallow.

In certain embodiments processed oils, such as blown oils, are the source of fatty acids useful herein. While vegetable oils are preferred sources of fatty acids for practicing disclosed embodiments of the present process, fatty acids also are available from animal fats including, without limitation, lard and fish oils, such as sardine oil and herring oil, and the like. As noted above, in certain embodiments a desired fatty acid or fatty acid precursor is produced by a plant or animal found in nature. However, particular fatty acids or fatty acid precursors are advantageously available from genetically modified organisms, such as genetically modified plants, particularly genetically modified algae. Such genetically modified organisms are designed to produce a desired fatty acid or fatty acid precursor biosynthetically or to produce increased amounts of such compounds.

Alkyl oleates and alkyl erucates are fatty acid esters that are often major components in biodiesel produced by the transesterification of alcohol and vegetable oils (preferably the alkyls are a $C_1$ to $C_{30}$ alkyl group, alternately a $C_1$ to $C_{20}$ alkyl group). Biodiesel compositions that are particularly useful in this invention are those which have high concentrations of alkyl oleate and alkyl erucate esters. These fatty acid esters preferably have one site of unsaturation such that cross-metathesis with ethylene yields 1-decene as the coproduct. Biodiesel compositions that are particularly useful are those produced from vegetable oils such as canola, rapeseed oil, palm oil, and other high oleate oil, high erucate oils. Particularly preferred vegetable oils include those having at least 50% (on a molar basis) combined oleic and erucic fatty acid chains of all fatty acid chains, preferably 60%, preferably 70%, preferably 80%, preferably 90%.

In another embodiment, useful fatty acid ester containing mixtures include those having at least 50% (on a molar basis) alkyl oleate fatty acid esters, preferably 60% of alkyl oleate fatty acid esters, preferably 70% of alkyl oleate fatty acid esters, preferably 80% of alkyl oleate fatty acid esters, preferably 90% of alkyl oleate fatty acid esters.

In another embodiment, useful fatty acid ester containing mixtures include those having at least 50% (on a molar basis) alkyl erucate fatty acid esters, preferably 60% of alkyl erucate fatty acid esters, preferably 70% of alkyl erucate fatty acid esters, preferably 80% of alkyl erucate fatty acid esters, preferably 90% of alkyl erucate fatty acid esters.

In another embodiment, useful fatty acid ester containing mixtures include those having at least 50% (on a molar basis) combined oleic and erucic fatty acid esters of all fatty acid ester chains, preferably 60%, preferably 70%, preferably 80%, preferably 90%.

Isomerization

In another embodiment, the feed material is first isomerized, then combined with a metathesis catalyst as described herein. For example, the processes disclosed herein may comprise providing a feed material (typically a fatty acid or fatty acid derivative), isomerizing a site of unsaturation in the feed material (typically a fatty acid or fatty acid derivative) to produce an isomerized feed material (typically a fatty acid or fatty acid derivative), and then contacting the isomerized material with an alkene in the presence of a metathesis catalyst. The isomerized material can be produced by isomerization with or without subsequent esterification or transesterification. Isomerization can be catalyzed by known biochemical or chemical techniques. For example, an isomerase enzyme, such as a linoleate isomerase, can be used to isomerize linoleic acid from the cis 9, cis 12 isomer to the cis 9, trans 11 isomer. This isomerization process is stereospecific; however, nonstereospecific processes can be used because both cis and trans isomers are suitable for metathesis. For example, an alternative process employs a chemical isomerization catalyst, such as an acidic or basic catalyst, can be used to isomerize an unsaturated feed material (typically a fatty acid or fatty acid derivative) having a site of unsaturation at one location in the molecule into an isomerized, feed material (typically a fatty acid or fatty acid derivative) having a site of unsaturation at a different location in the molecule. Metal or organometallic catalysts also can be used to isomerize an unsaturated feed material (typically a fatty acid or fatty acid derivative). For example, nickel catalysts are known to catalyze positional isomerization of unsaturated sites in fatty acid derivatives. Similarly, esterification, transesterification, reduction, oxidation and/or other modifications of the starting compound or products, such as a fatty acid or fatty acid derivative, can be catalyzed by biochemical or chemical techniques. For example, a fatty acid or fatty acid derivative can be modified by a lipase, esterase, reductase, or other enzyme before or after isomerization. In another embodiment the isomerization described above may be practiced with any triacylglycerides, biodiesel, fatty acids, fatty acid esters, and/or fatty acid alkyl esters described herein, typically before contacting with the metathesis catalyst.

Metathesis Catalyst Compounds

In a preferred embodiment, the metathesis catalyst compound is represented by the Formula (I):

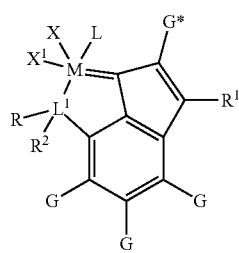

Formula (I)

where:

M is a Group 8 metal, preferably Ru or Os, preferably Ru;

X and $X^1$ are, independently, any anionic ligand, preferably a halide (preferably Cl), an alkoxide, aryloxide, or an alkyl sulfonate, or X and $X^1$ may be joined to form a dianionic group and may form single ring of up to 30 non-hydrogen atoms or a multinuclear ring system of up to 30 non-hydrogen atoms;

L is a neutral two electron donor, preferably a phosphine or an N-heterocyclic carbene or a cyclic alkyl amino carbene;

$L^1$ is a heteroatom selected from the group consisting of N or P, preferably N;

L and X may be joined to form a multidentate monoanionic group and may form single ring of up to 30 non-hydrogen atoms or a multinuclear ring system of up to 30 non-hydrogen atoms;

R is a $C_1$ to $C_{30}$ hydrocarbyl or a $C_1$ to $C_{30}$ substituted hydrocarbyl;

G* is selected from the group consisting of hydrogen, a $C_1$ to $C_{30}$ hydrocarbyl, and a $C_1$ to $C_{30}$ substituted hydrocarbyl, preferably an alkyl or substituted alkyl or hydrogen, preferably fluorinated alkyls or hydrogen;

$R^1$ is selected from the group consisting of hydrogen, a $C_1$ to $C_{30}$ hydrocarbyl, and a $C_1$ to $C_{30}$ substituted hydrocarbyl, preferably methoxy-substituted phenyl, preferably 3,5-substituted phenyl, preferably 3,5-dimethoxyphenyl;

$R^2$ is hydrogen, a $C_1$ to $C_{30}$ hydrocarbyl, or a $C_1$ to $C_{30}$ substituted hydrocarbyl, preferably methoxy-substituted phenyl, preferably 3,5-substituted phenyl, preferably 3,5-dimethoxyphenyl; and each G is, independently, selected from the group consisting of hydrogen, halogen, a $C_1$ to $C_{30}$ hydrocarbyl, and a $C_1$ to $C_{30}$ substituted hydrocarbyl hydrogen, (preferably a $C_1$ to $C_{30}$ alkyl or a substituted $C_1$ to $C_{30}$ alkyl, or a $C_5$ to $C_{30}$ aryl or a substituted $C_5$ to $C_{30}$ aryl).

For purposes of this invention and claims thereto, a "Group 8 metal" is an element from Group 8 of the Periodic Table, as referenced by the IUPAC in *Nomenclature of Inorganic Chemistry: Recommendations* 1990, G. J. Leigh, Editor, Blackwell Scientific Publications, 1990.

For purposes of this invention and claims thereto a substituted hydrocarbyl is a radical made of carbon and hydrogen where at least one hydrogen is replaced by a heteroatom. For purposes of this invention and claims thereto a substituted alkyl or aryl group is a radical made of carbon and hydrogen where at least one hydrogen is replaced by a heteroatom or a linear, branched, or cyclic substituted or unsubstituted hydrocarbyl group having 1 to 30 carbon atoms.

For purposes of this invention and claims thereto, "alkoxides" include those where the alkyl group is a $C_1$ to $C_{10}$ hydrocarbyl. The alkyl group may be straight chain or branched. Preferred alkoxides include a $C_1$ to $C_{10}$ alkyl group, preferably methyl, ethyl, propyl, butyl, or isopropyl. Preferred alkoxides include those where the alkyl group is a phenol, substituted phenol (where the phenol may be substituted with up to 1, 2, 3, 4, or 5 $C_1$ to $C_{12}$ hydrocarbyl groups) or a $C_1$ to $C_{10}$ hydrocarbyl, preferably a $C_1$ to $C_{10}$ alkyl group, preferably methyl, ethyl, propyl, butyl, or phenyl.

Preferred alkyl sulfonates are represented by the Formula (II):

Formula (II)

where $R^{2*}$ is a $C_1$ to $C_{30}$ hydrocarbyl group, fluoro-substituted carbyl group, chloro-substituted carbyl group, aryl group, or substituted aryl group, preferably a $C_1$ to $C_{12}$ alkyl or aryl group, preferably trifluoromethyl, methyl, phenyl, para-methyl-phenyl.

For purposes of this invention and claims thereto, "aryloxides" include those where the aryl group is a phenol or naphthalene, or substituted phenol or substituted naphthalene, where the phenol or naphthalene may be substituted with one or more substituents. (Substituted meaning that a hydrogen group is replaced by a heteroatom or by a linear, branched, or cyclic hydrocarbyl group having 1 to 30 carbon atoms.) Suitable substituents are independently selected and may comprise halogen, $C_1$ to $C_{12}$ hydrocarbyl groups, substituted $C_1$ to $C_{12}$ hydrocarbyl groups, preferably halogen, trifluoromethyl, amino, alkyl, alkoxy, alkylcarbonyl, cyano, carbamoyl, alkoxycarbamoyl, methylendioxy, carboxyl, alkoxycarbonyl, aminocarbonyl, alkyaminocarbonyl, dialkylaminocarbonyl, hydroxy, nitro, and the like, more preferably phenyl, chlorophenyl, trifluoromethylphenyl, chlorofluorophenyl, aminophenyl, methylcarbonylphenyl, methoxyphenyl, methylendioxyphenyl, 1-naphthyl and 2-naphthyl.

For purposes of this invention and claims thereto, "phosphines" may be represented by the formula $PR_3$, wherein R is independently selected from the group comprising hydrogen, $C_1$ to $C_{12}$ hydrocarbyl groups, substituted $C_1$ to $C_{12}$ hydrocarbyl groups, and halides.

For purposes of this invention and claims thereto, "N-heterocyclic carbenes" (NHCs) are represented by the Formula (III):

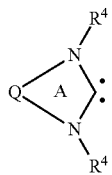

Formula (III)

wherein the ring A is a 4-, 5-, 6-, or 7-membered ring, and Q is a linking group comprising from one to four linked vertex atoms selected from the group comprising C, O, N, B, Al, P, S, and Si with available valences optionally occupied by hydrogen, oxo or R-substituents, wherein R is independently selected from the group comprising $C_1$ to $C_{12}$ hydrocarbyl groups, substituted $C_1$ to $C_{12}$ hydrocarbyl groups, and halides, and each $R^4$ is independently a hydrocarbyl group or substituted hydrocarbyl group having 1 to 40 carbon atoms, preferably methyl, ethyl, propyl, butyl (including isobutyl and n-butyl), pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, tolulyl, chlorophenyl, phenol, or substituted phenol.

Some particularly useful N-heterocyclic carbenes may be represented by the Formula (IV) and (V):

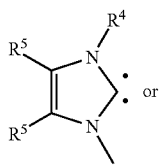

Formula (IV)

or

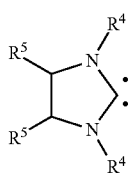

Formula (V)

where
each $R^4$ is independently a hydrocarbyl group or substituted hydrocarbyl group having 1 to 40 carbon atoms, preferably methyl, ethyl, propyl, butyl (including isobutyl and n-butyl), pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, tolulyl, chlorophenyl, phenol, substituted phenol, or $CH_2C(CH_3)_3$; and each $R^5$ is independently a hydrogen, a halogen, a $C_1$ to $C_{12}$ hydrocarbyl group, or a $C_1$ to $C_{12}$ substituted hydrocarbyl group, preferably hydrogen, bromine, chlorine, methyl, ethyl, propyl, butyl, or aryl.

In other useful embodiments, one of the N groups bound to the carbene in Formulae (IV) or (V) is replaced with another heteroatom, preferably S, O, or P, preferably an S heteroatom. Other useful N-heterocyclic carbenes include the compounds described in Hermann, W. A. *Chem. Eur. J.* 1996, 2, 772 and 1627; Enders, D. et al., *Angew. Chem. Int. Ed.* 1995, 34, 1021; Alder R. W., *Angew. Chem. Int. Ed.* 1996, 35, 1121; and Bertrand, G. et al., *Chem. Rev.* 2000, 100, 39.

For purposes of this invention and claims thereto, "cyclic alkyl amino carbenes" (CAACs) are represented by the Formula (VI):

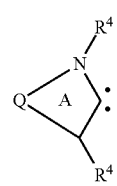

Formula (VI)

wherein the ring A is a 4-, 5-, 6-, or 7-membered ring, and Q is a linking group comprising from one to four linked vertex atoms selected from the group comprising C, O, N, B, Al, P, S, and Si with available valences optionally occupied by hydrogen, oxo or R-substituents, wherein R is independently selected from the group comprising $C_1$ to $C_{12}$ hydrocarbyl groups, substituted $C_1$ to $C_{12}$ hydrocarbyl groups, and halides, and each $R^4$ is independently a hydrocarbyl group or substituted hydrocarbyl group having 1 to 40 carbon atoms, preferably methyl, ethyl, propyl, butyl (including isobutyl and n-butyl), pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, tolulyl, chlorophenyl, phenol, or substituted phenol.

Some particularly useful CAACs include:

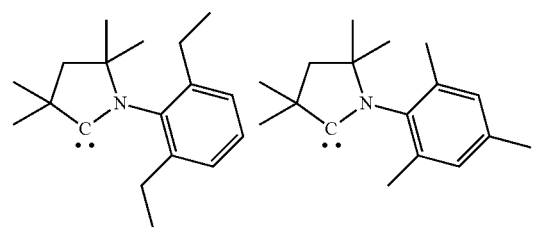

Other useful CAACs include the compounds described in U.S. Pat. No. 7,312,331 and Bertrand et al, *Angew. Chem. Int. Ed.* 2005, 44, 7236-7239.

Some preferred metathesis catalyst compounds include:

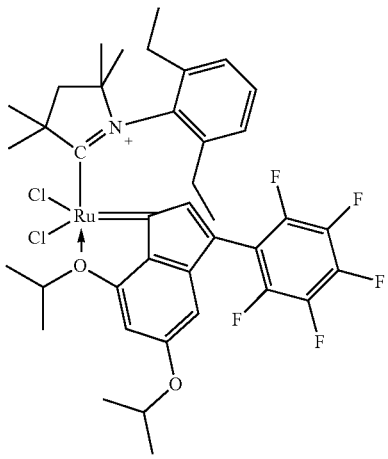

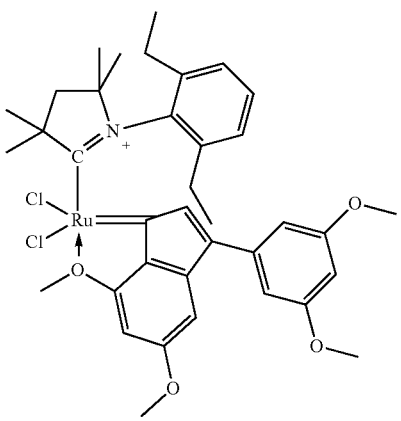

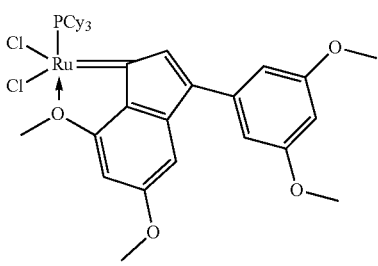

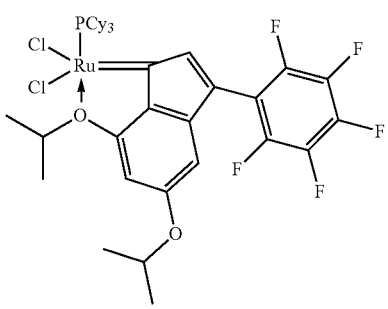

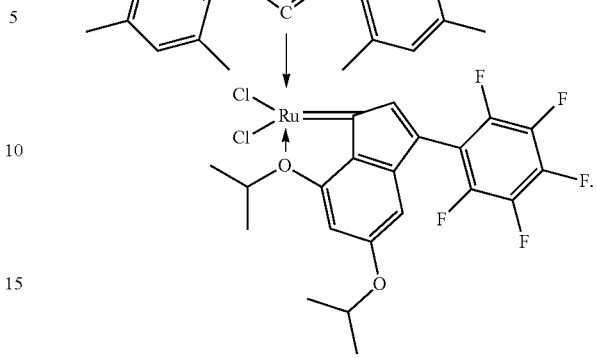

Although the catalyst compounds herein are described with respect to olefin cross-metathesis, one of skill in the art will appreciate that the catalyst compounds of this invention may be suitable for any metathesis reaction, including, but not limited to, ring-closing metathesis, enyne metathesis, acyclic diene metathesis, and so on.

In certain embodiments, the catalyst compound employed in the process of this invention may be bound to or deposited on a solid catalyst support. The solid catalyst support will render the catalyst compound heterogeneous, which will simplify catalyst recovery. In addition, the catalyst support may increase catalyst strength and attrition resistance. Suitable catalyst supports include, without limitation, silicas, aluminas, silica-aluminas, aluminosilicates, including zeolites and other crystalline porousaluminosilicates; as well as titanias, zirconia, magnesium oxide, carbon, and cross-linked, reticular polymeric resins, such as functionalized cross-linked polystyrenes, e.g., chloromethyl-functionalized cross-linked polystyrenes. The catalyst compound may be deposited onto the support by any method known to those skilled in the art, including, for example, impregnation, ion-exchange, deposition-precipitation, and vapor deposition. Alternatively, the catalyst compound may be chemically bound to the support via one or more covalent chemical bonds, for example, the catalyst compound may be immobilized by one or more covalent bonds with one or more of substituents of the indenylene ligand.

If a catalyst support is used, the catalyst compound may be loaded onto the catalyst support in any amount, provided that the metathesis process of this invention proceeds to the desired metathesis products. Generally, the catalyst compound is loaded onto the support in an amount that is greater than about 0.01 wt % of the Group 8 metal, and preferably greater than about 0.05 wt % of the Group 8 metal, based on the total weight of the catalyst compound plus support. Generally, the catalyst compound is loaded onto the support in an amount that is less than about 20 wt % of the Group 8 metal, and preferably less than about 10 wt % of the Group 8 metal, based on the total weight of the catalyst compound and support.

Synthesis of Metathesis Catalyst Compounds

The catalyst compounds described herein may be synthesized by any methods known to those skilled in the art.

Representative methods of synthesizing the Group 8 catalyst compound of the type described herein include, for example, treating a solution of the ligand complex in a suitable solvent, such as THF, with a reactant complex of a Group 8 metal, such as dichloro-bis-(triphenylphosphine)ruthenium (II) and acetyl chloride. The mixture may be heated, for example to reflux, for a time period appropriate to yield the desired chelating indenylene catalyst compound. Typically, removal of the volatiles affords the Group 8 chelating indenylene catalyst compound, which may optionally be purified by suitable chromatographical methods, as known in the art.

A phosphine ligand, such as tricyclohexylphosphine may be added thereafter, if desired. The reaction conditions typically include mixing the Group 8 reactant catalyst compound and the preferred phosphine ligand in a suitable solvent, such as benzene, for a time sufficient to effectuate the phosphine ligand exchange, at a suitable temperature typically ambient. Copper (I) chloride is then added in excess and removal of the volatiles from resultant slurry typically affords the Group 8 chelating indenylene catalyst compound comprising the more preferred phosphine ligand.

While the present invention describes a variety of transition metal complexes useful in catalyzing metathesis reactions, it should be noted that such complexes may be formed in situ. Accordingly, additional ligands may be added to a reaction solution as separate compounds, or may be complexed to the metal center to form a metal-ligand complex prior to introduction to the reaction.

Alpha-Olefin Products of the Metathesis Reaction.

In a preferred embodiment, the processes described herein produce an alpha olefin, preferably a linear alpha-olefin, which contains at least one more carbon than the alkene used in the reaction to make the alpha-olefin.

In another embodiment, the processes described herein produce a blend of an alpha olefin and an ester-functionalized alpha olefin. Generally, a mixture of non-ester-containing alpha olefins will be produced due to the presence of mono-, di-, and tri-unsubstituted fatty acid chains. The major alpha olefin products are typically 1-decene, 1-heptene, and 1-butene. The major ester-containing alpha olefin product is typically methyl 9-decenoate.

In a preferred embodiment, the alpha olefin produced herein is 1-decene. Typically the co-product of 1-decene is an ester.

In a preferred embodiment, the major alpha olefin produced herein is 1-decene. Typically, the coproduct of 1-decene is an ester.

In a preferred embodiment, ethylene and methyl oleate are combined with the metathesis catalysts described herein (such as triphenylphosphinedichlorideruthenium(3-(3,5-dimethoxyphenyl)-6,8-dimethoxyinden-1-ylidene); triphenylphosphinedichlorideruthenium(3-pentafluorophenyl-6,8-diisopropoxyinden-1-ylidene); and/or tricyclohexylphosphinedichlorideruthenium (3-pentafluorophenyl-6,8-diisopropoxyinden-1-ylidene)) to produce 1-decene and methyl 9-decenoate.

Separation of the 1-olefin (such as the 1-decene) from the ester may be by means typically known in the art such as distillation or filtration.

The linear alpha-olefin cross-metathesis product (such as 1-decene or a mixture of $C_8$, $C_{10}$, $C_{12}$ linear alpha olefins) is then separated from any esters present and preferably used to make poly-alpha-olefins (PAOs). Specifically, PAOs may be produced by the polymerization of olefin feed in the presence of a catalyst such as $AlCl_3$, $BF_3$, or $BF_3$ complexes. Processes for the production of PAOs are disclosed, for example, in the following patents: U.S. Pat. Nos. 3,149,178; 3,382,291; 3,742,082; 3,769,363; 3,780,128; 4,172,855; and 4,956,122, which are fully incorporated by reference. PAOs are also discussed in Will, J. G. *Lubrication Fundamentals*, Marcel Dekker: New York, 1980. Certain high viscosity index PAO's may also be conveniently made by the polymerization of an alpha-olefin in the presence of a polymerization catalyst such as Friedel-Crafts catalysts. These include, for example, aluminum trichloride, boron trifluoride, aluminum trichloride or boron trifluoride promoted with water, with alcohols such as ethanol, propanol, or butanol, with carboxylic acids, or with esters such as ethyl acetate or ethyl propionate or ether such as diethyl ether, diisopropyl ether, etc., see for example, the methods disclosed by U.S. Pat. Nos. 4,149,178; 3,382,29; 3,742,082; 3,769,363 (Brennan); U.S. Pat. Nos. 3,876,720; 4,239,930; 4,367,352; 4,413,156; 4,434,408; 4,910,355; 4,956,122; 5,068,487; 4,827,073; 4,827,064; 4,967,032; 4,926,004; and 4,914,254. PAO's can also be made using various metallocene catalyst systems. Examples include U.S. Pat. Nos. 6,706,828; 5,688,887; 6,043,401; 6,548,724; 5,087,788; 6,414,090; 6,414,091; 4,704,491; 6,133,209; 6,713,438; WO 96/23751; WO 03/020856; and EP 0 613 873.

PAOs are often used as additives and base stocks for lubricants, among other things. Additional information on the use of PAO's in the formulations of full synthetic, semi-synthetic or part synthetic lubricant or functional fluids can be found in "Synthetic Lubricants and High-Performance Functional Fluids", 2nd Ed. L. Rudnick, etc. Marcel Dekker, Inc., N.Y. (1999). Additional information on additives used in product formulation can be found in "Lubricants and Lubrications, Ed. By T. Mang and W. Dresel, by Wiley-VCH GmbH, Weinheim 2001.

In another embodiment this invention relates to:

1. A metathesis catalyst compound represented by the formula:

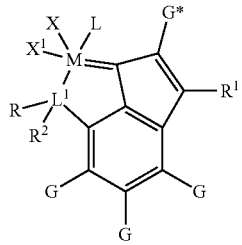

wherein M is a Group 8 metal; X and $X^1$ are anionic ligands; L is a neutral two electron donor; $L^1$ is N or P, preferably N; R is a $C_1$ to $C_{30}$ hydrocarbyl or a $C_1$ to $C_{30}$ substituted hydrocarbyl; $G^*$ is selected from the group consisting of hydrogen, a $C_1$ to $C_{30}$ hydrocarbyl, and a $C_1$ to $C_{30}$ substituted hydrocarbyl; $R^1$ is selected from the group consisting of hydrogen, a $C_1$ to $C_{30}$ hydrocarbyl, and a $C_1$ to $C_{30}$ substituted hydrocarbyl; $R^2$ is hydrogen, a $C_1$ to $C_{30}$ hydrocarbyl or a $C_1$ to $C_{30}$ substituted hydrocarbyl, preferably methoxy-substituted phenyl, preferably 3,5-substituted phenyl, preferably 3,5-dimethoxyphenyl; and G is independently selected from the group consisting of hydrogen, halogen, $C_1$ to $C_{30}$ hydrocarbyls and $C_1$ to $C_{30}$ substituted hydrocarbyls.

2. The catalyst compound of paragraph 1, wherein M is Ru.

3. The catalyst compound of paragraph 1 or 2, wherein X and $X^1$ are, independently, a halogen, an alkoxide, aryloxide, or an alkyl sulfonate.

4. The catalyst compound of any of paragraphs 1 to 3, wherein at least of X and $X^1$ is chloride, preferably both X and $X^1$ are chloride.

5. The catalyst compound of any of paragraphs 1 to 4, wherein $L^1$ is N.

6. The catalyst compound of any of paragraphs 1 to 5, wherein L is selected from the group consisting of a phosphine, an N-heterocyclic carbene, and a cyclic alkyl amino carbene.

7. The catalyst compound of any of paragraphs 1 to 6, wherein G* is selected from the group consisting of hydrogen, an alkyl, and substituted alkyl.
8. The catalyst compound of any of paragraphs 1 to 7, wherein each G is independently, a $C_1$ to $C_{30}$ substituted or unsubstituted alkyl, or a substituted or unsubstituted $C_4$ to $C_{30}$ aryl.
9. The catalyst compound of any of paragraphs 1 to 8, wherein $R^1$ is a methoxy substituted phenyl.
10. The catalyst compound of any of paragraphs 1 to 9, wherein L and X are joined to form a multidentate monoanionic group or a dianionic group and may form a single ring of up to 30 non-hydrogen atoms or a multinuclear ring system of up to 30 non-hydrogen atoms.
11. A process to produce alpha-olefin comprising contacting a feed material (such as a feed oil) with the catalyst compound of any of paragraphs 1 to 10.
12. The process of paragraph 11, wherein the feed material is selected from the group consisting of canola oil, corn oil, soybean oil, rapeseed oil, algae oil, peanut oil, mustard oil, sunflower oil, tung oil, perilla oil, grapeseed oil, linseed oil, safflower oil, pumpkin oil, palm oil, Jathropa oil, high-oleic soybean oil, high-oleic safflower oil, high-oleic sunflower oil, mixtures of animal and vegetable fats and oils, castor bean oil, dehydrated castor bean oil, cucumber oil, poppyseed oil, flaxseed oil, lesquerella oil, walnut oil, cottonseed oil, meadowfoam, tuna oil, sesame oils, and mixtures thereof.
13. The process of paragraph 11, wherein the feed material is selected from the group consisting of palm oil and algae oil.
14. A process to produce alpha-olefin comprising contacting a triacylglyceride with an alkene and the catalyst compound of any of paragraphs 1 to 10, preferably wherein the alpha olefin produced has at least one more carbon atom than the alkene.
15. The process of paragraph 14, wherein the triacylglyceride is contacted with alcohol and converted to a fatty acid ester or fatty acid alkyl ester prior to contacting with the catalyst compound of any of paragraphs 1 to 10.
16. The process of paragraph 14, wherein the triacylglyceride is contacted with water or an alkaline reagent and converted to a fatty acid prior to contacting with the catalyst compound of any of paragraphs 1 to 10.
17. A process to produce alpha-olefin comprising contacting an unsaturated fatty acid with an alkene and the catalyst compound of any of paragraphs 1 to 10, preferably wherein the alpha olefin produced has at least one more carbon atom than the alkene.
18. A process to produce alpha-olefin comprising contacting a triacylglyceride with the catalyst compound of any of paragraphs 1 to 10, preferably wherein the alpha olefin produced has at least one more carbon atom than the alkene.
19. A process to produce alpha-olefin comprising contacting an unsaturated fatty acid ester and/or unsaturated fatty acid alkyl ester with an alkene and the catalyst compound of any of paragraphs 1 to 10, preferably wherein the alpha olefin produced has at least one more carbon atom than the alkene.
20. The process of any of paragraphs 11 to 19, wherein the alpha olefin is a linear alpha-olefin having 4 to 24 carbon atoms.
21. The process of any of paragraphs 11 to 20, wherein the alkene is ethylene, propylene, butene, hexene, or octene.
22. The process of any of paragraphs 19 to 21, where the fatty acid ester is a fatty acid methyl ester.
23. The process of any of paragraphs 14 to 22, wherein the triacylglyceride, fatty acid, fatty acid alkyl ester, and fatty acid ester is derived from biodiesel.
24. The process of any of paragraphs 11 to 23, wherein the alpha-olefin is butene-1, decene-1, and/or heptene-1.
25. The process of any of paragraphs 11 to 24, wherein the productivity of the process is at least 200 g of linear alpha-olefin per mmol of catalyst per hour.
26. The process of any of paragraphs 11 to 25, wherein the selectivity of the process is at least 20 wt % linear alpha-olefin, based upon the weight to the material exiting the reactor.
27. The process of any of paragraphs 11 to 26, wherein the turnover number, defined as the moles of alpha olefin formed per mol of catalyst, of the process is at least 10,000.
28. The process of any of paragraphs 11 to 27, wherein the yield, when converting unsaturated fatty acids, unsaturated fatty acid esters, unsaturated fatty acid alkyl esters or mixtures thereof, is 30% or more, said yield being defined as the moles of alpha olefin formed per mol of unsaturated fatty acids, unsaturated fatty acid esters, unsaturated fatty acid alkyl esters or mixtures thereof introduced into the reactor.
29. The process of any of paragraphs 11 to 27, wherein the yield, when converting TAGs as represented in the formula below, is 30% or more, said yield being defined as the moles of alpha olefin formed divided by (the moles of unsaturated $R^a$+moles of unsaturated $R^b$+moles of unsaturated $R^c$) introduced into the reactor,

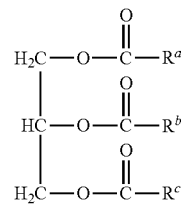

where $R^a$, $R^b$, and $R^c$ each, independently, represent a saturated or unsaturated hydrocarbon chain.
30. The process of paragraph 28, wherein the yield is 60% or more.
31. A process to produce $C_4$ to $C_{24}$ linear alpha-olefin comprising contacting a feed material with an alkene selected from the group consisting of ethylene, propylene butene, pentene, hexene, heptene, octene, nonene and mixtures thereof and a metathesis catalyst compound of any of paragraphs 1 to 10, wherein the feed material is a triacylglyceride, fatty acid, fatty acid alkyl ester, and/or fatty acid ester derived from seed oil.
32. The process of claim 31, wherein the alkene is ethylene; the alpha olefin is 1-butene, 1-heptene, and/or 1-decene; and the feed material is a fatty acid methyl ester and/or fatty acid ester.

Experimental Section

For purposes of this invention and the claims thereto, Et is ethyl, Me is methyl, Ph is phenyl, Cy is cyclohexyl, THF is tetrahydrofuran, AcCl is acetyl chloride, DMF is dimethylformamide, and TLC is thin layer chromatography.

Typical dry-box procedures for synthesis of air-sensitive compounds were followed including using dried glassware (90° C., 4 hours) and anhydrous solvents purchased from Sigma Aldrich (St. Louis, Mo.) which were further dried over 3 A sieves. All reagents were purchased from Sigma-Aldrich, unless otherwise noted. $^1H$, $^{13}C$, and $^{31}P$ spectra were recorded on Bruker 250 and 500 spectrometers. IR data was recorded on Bruker Tensor 27 FT-IR spectrometer. Yields of metathesis product and catalyst turnover numbers were calculated from data recorded on an Agilent 6890 GC spectrometer as shown below.

Typically, a sample of the metathesis product will be taken and analyzed by GC. An internal standard, usually tetradecane, is used to derive the amount of metathesis product that is obtained. The amount of metathesis product is calculated from the area under the desired peak on the GC trace, relative to the internal standard.

Yield is reported as a percentage and defined as 100×[micromoles of metathesis products obtained by GC]/[micromoles of feed material weighed into reactor]. Selectivity is reported as a percentage and is defined as 100×[area under the peak of desired metathesis products]/[sum of peak areas of cross-metathesis and the homometathesis products]. Catalyst turnovers for production of the metathesis products is defined as the [micromoles of metathesis product]/[micromoles of catalyst].

In a particular embodiment, the metathesis of methyl oleate with ethylene will yield co-metathesis products of 1-decene and methyl-9-decenoate. In addition to the desired products, the methyl oleate may homometathesize to produce small amounts of 9-octadecene, a less desirable product, and 1,18-dimethyl-9-octadecenedioate, a second less desirable product. Yield is defined as 100×[micromoles of ethenolysis products obtained from the GC]/[micromoles of methyl oleate weighed into reactor]. 1-decene selectivity is shown as a percentage and is defined as 100×[GC peak area of 1-decene & methyl-9-decenoate]/[sum of GC peak areas of 1-decene, methyl-9-decenoate, and the homometathesis products, 9-octadecene, and 1,18-dimethyl-9-octadecenedioate]. Catalyst turnovers for production of the 1-decene is defined as the [micromoles of 1-decene obtained from the GC]/[micromoles of catalyst].

Examples

Synthetic protocols for representative alkylidene ligands and the corresponding ruthenium alkylidene complexes are as follows. Other alkylidene ligands and their respective metal complexes may be derived analogously.

Example 1

Synthesis of $(PPh_3)Cl_2Ru(3-3,5-dimethoxyphenyl-6,8-dimethoxyinden-1-ylidene)$ Bis(3,5-dimethoxyphenyl)methanol (A)

3,5-Dimethoxybenzaldehyde (5.0 g, 30 mmol) was dissolved in 150 mL THF in a 500 mL round bottom flask. 3,5-Dimethoxyphenyl magnesium chloride (1 M in THF, 45 mL) was added slowly. The reaction was heated at 40° C. for 4 hours then quenched with saturated ammonium chloride. The mixture was extracted with 3 portions of ether and the combined organic layers washed with brine, dried over anhydrous $MgSO_4$, then concentrated to a crude pale yellow solid which was carried forward to the next step: $^1H$ NMR (250 MHz, $C_6D_6$): δ 3.29 (d, J=5.0 Hz, 12H), 6.46 (m, 2H), 6.56 (m, 1H), 6.76 (m, 2H), 7.04 (t, J=8.2 Hz, 1H).

Bis(3,5-dimethoxyphenyl)methanone (B)

Pyridinium chlorochromate (PCC) (12.9 g, 30 mmol) was suspended in 30 mL dichloromethane in a 200 mL round bottom flask. Crude bis(3,5-dimethoxyphenyl)methanol from above (compound A) was suspended in 30 mL dichloromethane then added to the chromate suspension. The dark solution was allowed to stir at ambient temperature for 18 hours then diluted with ether. After decantation, the organic solution was washed twice with 1N NaOH, twice with 10% HCl, saturated $NaHCO_3$, and then with brine. It was dried over anhydrous $MgSO_4$, filtered and concentrated to give a brownish yellow solid. The brownish yellow solid was purified by column chromatography using 50% acetone/hexane as eluent giving the product as a yellow solid in 63% yield over 2 steps: IR (cm$^{-1}$): 2960, 2938, 2834, 1660, 1592, 1456, 1425, 1349, 1304, 1205, 1157, 1066, 744; $^1H$ NMR (250 MHz, $C_6D_6$): δ 3.21 (s, 12H), 6.67 (t, J=2.2 Hz, 2H), 7.21 (d, J=2.5 Hz, 4H); $^{13}C$ NMR (63 MHz, $C_6D_6$): 54.9 (4C), 105.3 (2C), 108.0 (4C), 140.2 (2C), 161.1 (4C), 195.2.

1,1-Bis(3,5-dimethoxyphenyl)prop-2-yn-1-ol (C)

In a 100 mL flask, bis(3,5-dimethoxy-phenyl)methanone (compound B, 1.2 g, 3.9 mmol) was dissolved in 20 mL diethyl ether. Approximately 5 mL THF was added to help solvate the ketone followed by the slow addition of ethynylmagnesium bromide (0.5 M in THF, 12 mL). The reaction was monitored by TLC and upon consumption of starting material, 2N HCl was added to the flask. The mixture was extracted 3 times with ethyl acetate and the combined organic layers were washed with brine, dried over anhydrous $MgSO_4$, filtered, and concentrated to give a yellow oil. Purification was achieved with column chromatography using a gradient of 30% to 50% acetone/hexane. The product was obtained as a pale yellow oil in 73% yield: $R_f$ 0.14 (30:70 acetone/hexane); IR (cm$^{-1}$): 3441, 3280, 2940, 2837, 1598, 1460, 1289, 1205, 1156, 1053, 834, 748, 689; $^1H$ NMR (250 MHz, $C_6D_6$): δ 2.38 (s, 1H), 2.94 (br s, 1H), 3.27 (s, 12H), 6.42 (t, J=2.5 Hz, 2H), 3.99 (d, J=2.5 Hz, 4H); $^{13}C$ NMR (63 MHz, $C_6D_6$): 54.8 (4C), 74.5, 75.3, 86.8, 100.1 (2C), 104.9 (4C), 147.6 (2C), 161.2 (4C).

Scheme 1: Synthesis of 1,1-bis(3,5-dimethoxyphenyl)prop-2-yn-1-ol (C)

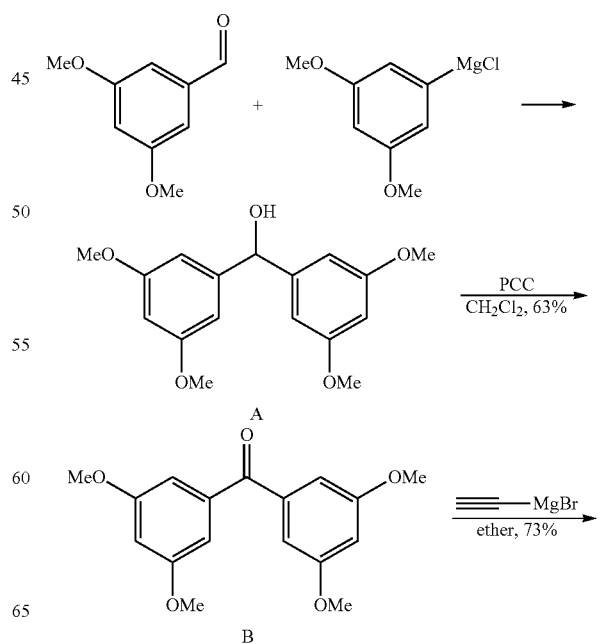

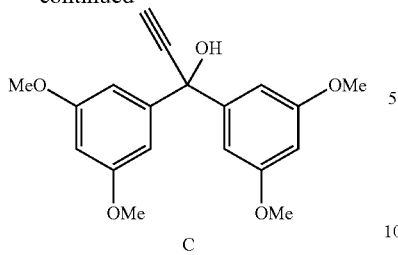

C (PPh₃)Cl₂Ru(3-3,5-dimethoxyphenyl-6,8-dimethoxyinden-1-ylidene) (D)

Acetyl chloride (5-10 µl) was added to a solution of (PPh₃)₃RuCl₂ (336 mg, 0.35 mmol) and 1,1 di(3,5-dimethoxy)phenyl 2-propyn-1-ol (compound C, 172 mg, 0.525 mmol) in 6 mL THF. The propynol was added as a 0.2 M solution in THF. The solution was allowed to reflux for 18 hours, after which the reaction flask was placed under high vacuum to remove the solvent. Isopropanol (12 mL) was added to the reaction flask and the purple material was removed from the walls by intense stirring overnight. The resulting suspension was filtered and washed with 5 mL of isopropanol followed by two pentane washes (5 mL each). Any remaining solvent was removed from the red-brown powder in vacuo at 60° C., yielding 240 mg (92%). The product was characterized by NMR spectra (¹H, ¹³C, and ³¹P). The results are as below.

¹H NMR (250 MHz, CD₂Cl₂, 30° C.): δ=7.4 (bt, 11H), 6.0-7.0 (m, 6H), 4.57 (s, 0.5H), 3.74-4.0 (m, 6H, R—OCH₃×2), 3.64 (s, 6H, R—OCH₃×2). ¹³C NMR (500 MHz, CD₂Cl₂, 30° C.): δ=289.7 (d, $J_{PC}$=100 Hz). ³¹P NMR (250 MHz, CD₂Cl₂, 30° C.): δ=54 ppm.

Scheme 2: Synthesis of (PPh₃)Cl₂Ru(3-3,5-dimethoxyphenyl-6,8-dimethoxyinden-1-ylidene) (D)

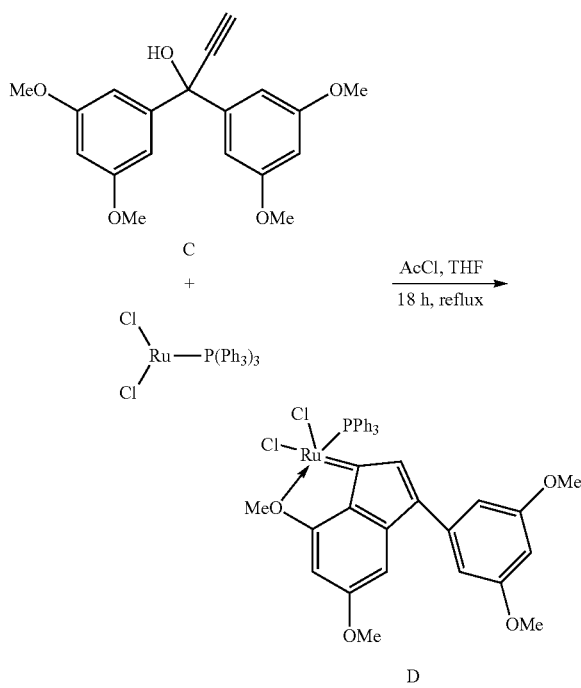

Example 2

Synthesis of (PPh₃)Cl₂Ru(3-pentafluorophenyl-6,8-diisopropoxyinden-1-ylidene) (J)

Isopropyl 3,5-diisopropoxybenzoate (E)

In a 1 L round bottom flask, 3,5-dihydroxybenzoic acid (10 g, 64 mmol), potassium carbonate (42 g, 260 mmol) and cesium carbonate (30 g, 92 mmol) were dissolved in 300 mL dimethylformamide. After stirring at ambient temperature for approximately 20 min, 2-iodopropane (43 g, 256 mmol) was added. The reaction was allowed to stir overnight, then quenched with water and extracted with three portions of ethyl acetate. The combined organic layers were washed twice with both water and brine, then dried (MgSO₄), filtered and concentrated to a yellow oil: $R_f$ 0.48 (30:70 acetone/hexane); IR (cm⁻¹): 2978, 2935, 1715, 1593, 1449, 1372, 1296, 1234, 1183, 1112, 1038, 769; ¹H NMR (250 MHz, C₆D₆): δ 1.07 (dd, J=6.7, 12.0 Hz, 18H), 4.20 (qn, J=6.2 Hz, 2H), 5.22 (qn, J=6.2 Hz, 1H), 6.75 (t, J=2.5 Hz, 1H), 7.56 (d, J=2.5 Hz, 2H); ¹³C NMR (63 MHz, C₆D₆): 23.7 (2C), 23.8 (4C), 70.2, 71.8 (2C), 110.9, 111.1 (2C), 135.5, 161.6 (2C), 167.9.

3,5-diisopropoxybenzoic acid (F)

Crude isopropoxybenzoate from above (compound E) was dissolved in 200 mL THF/H₂O (1:1) in a 500 mL flask. Excess lithium hydroxide (10 g) was added and the reaction refluxed for over 48 hours. The mixture was cooled, acidified with HCl to pH 2, then extracted with several portions of diethyl ether. The organic layers were washed with brine, dried over MgSO₄, and concentrated to a white solid in 55% yield over 2 steps: IR (cm⁻¹): 3064, 2978, 2933, 2639, 1693, 1594, 1300, 1158, 1114, 1040, 767; ¹H NMR (250 MHz, CD₃OD): δ 1.30 (dd, J=2.3, 5.9 Hz, 12H), 4.59 (qn, J=6.2 Hz, 2H), 6.61 (t, J=2.3 Hz, 1H), 7.10 (d, J=2.5 Hz, 2H); ¹³C NMR (63 MHz, CD₃OD): 22.2 (4C), 71.2 (2C), 109.8, 109.9, 133.8, 160.3 (2C), 169.7.

3,5-diisopropoxy-N-methoxy-N-methylbenzamide (G)

Diisopropoxybenzoic acid (compound F, 10 g, 41 mmol) was dissolved in benzene (100 mL) in a 500 mL round bottom flask. Thionyl chloride (12.2 mL, 168 mmol) was added and the reaction heated at reflux for 1 hour. The mixture was then cooled to room temperature and concentrated under reduced pressure. The resulting residue was redissolved in dichloromethane and concentrated again to give 3,5-diisopropoxybenzoyl chloride. In a separate 200 mL flask, N,O-dimethylhydroxylamine-HCl (4.0 g, 42 mmol) was suspended in 80 mL dichloromethane at 0° C. Triethylamine (12.4 mL, 88 mmol) was added slowly, followed by crude 3,5-diisopropoxybenzoyl chloride. The reaction flask was allowed to warm to ambient temperature and stirred overnight. The reaction was quenched with water and extracted with three portions of dichloromethane. The combined organic layers were washed with brine, dried over MgSO₄, filtered and concentrated under reduced pressure. Purification of the resulting brown oil by column chromatography (30% acetone/hexane) gave the Weinreb amide (compound G) as a yellow oil in 60% yield from 3,5-dihydroxybenzoic acid: $R_f$ 0.33 (30:70 acetone/hexane); IR (cm⁻¹): 2977, 1647, 1590, 1441, 1374, 1184, 1155, 1113, 1037, 964; ¹H NMR (250 MHz, C₆D₆): δ 1.06 (dd, J=2.5, 5.9 Hz, 12H), 3.00 (s, 3H), 3.05 (s, 3H), 4.19

(qn, J=6.2 Hz, 2H), 6.69 (t, J=2.5 Hz, 1H), 7.10 (d, J=2.5 Hz, 2H); $^{13}$C NMR (63 MHz, C$_6$D$_6$): 21.9 (4C), 33.4, 60.4, 69.8 (2C), 106.6, 108.1 (2C), 137.0, 159.3 (2C), 169.8.

3,5-diisopropoxyphenylperfluorophenylmethanone (H)

In a 200 mL round bottom flask, the Weinreb amide (compound G, 1 g, 3.5 mmol) was dissolved in ether and cooled. Pentafluorophenylmagnesium bromide (0.5 M in THF, 8.52 mL) was added slowly and the reaction stirred under ambient conditions overnight. The mixture was quenched with saturated ammonium chloride and extracted with three portions of ether. Combined organic layers were washed with brine, dried over anhydrous MgSO$_4$, filtered and concentrated to give a dark brown oil which upon column chromatography (40% acetone/hexane) crystallized to the desired ketone in 46% yield: R$_f$ 0.60 (30:70 acetone/hexane); IR (cm$^{-1}$): 2980, 1682, 1588, 1501, 1320, 1185, 1160, 1113, 991, 770; $^1$H NMR (250 MHz, C$_6$D$_6$): δ 1.02 (d, J=5.0 Hz, 12H), 4.10 (qn, J=7.5 Hz, 2H), 6.66 (t, J=2.2 Hz, 1H), 7.13 (d, J=2.2 Hz, 2H); $^{13}$C NMR (63 MHz, C$_6$D$_6$): 21.6 (4C), 70.2 (2C), 109.1 (2C), 109.8, 138.5, 160.1 (2C), 184.9.

1-(3,5-diisopropoxyphenyl)-1-perfluorophenylprop-2-yn-1-ol (I)

The above methanone (compound H, 3.2 g, 8.2 mmol) was dissolved in 40 mL ether in a 100 mL round bottom flask. Ethynylmagnesium bromide (0.5 M in THF, 24.6 mL) was added slowly and the reaction stirred overnight. The reaction was quenched with saturated ammonium chloride and extracted with three portions of ether. Combined organic layers were washed with brine, dried over anhydrous MgSO$_4$, filtered and concentrated. The resulting oil was purified by column chromatography (40% acetone/hexane) and gave the desired propargyl alcohol as a dark brown oil in 47% yield: R$_f$ 0.15 (40:60 acetone/hexane); IR (cm$^{-1}$): 3423, 3309, 2979, 1595, 1524, 1492, 1115, 985; $^1$H NMR (250 MHz, C$_6$D$_6$): δ 1.10 (d, J=7.5 Hz, 12H), 2.29 (s, 1H), 2.67 (s, 1H), 4.26 (qn, J=6.7 Hz, 2H), 6.54 (t, J=2.3 Hz, 1H), 7.11 (d, J=2.5 Hz, 2H); $^{13}$C NMR (63 MHz, C$_6$D$_6$): 21.9 (4C), 69.8 (2C), 71.9, 75.7, 83.7, 103.6, 105.8 (2C), 145.2, 159.8 (2C).

Scheme 3: Synthesis of 1-(3,5-diisopropoxyphenyl)-1-perfluorophenylprop-2-yn-1-ol (I)

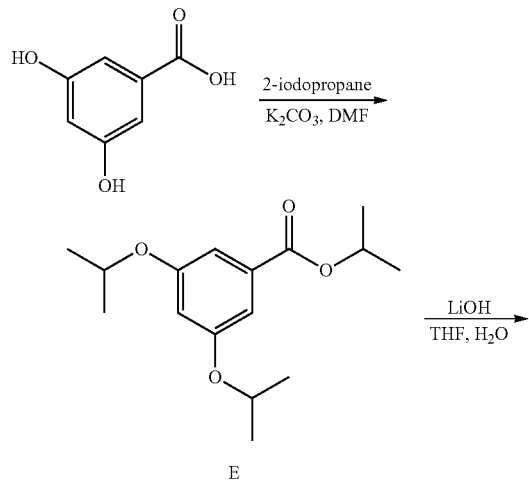

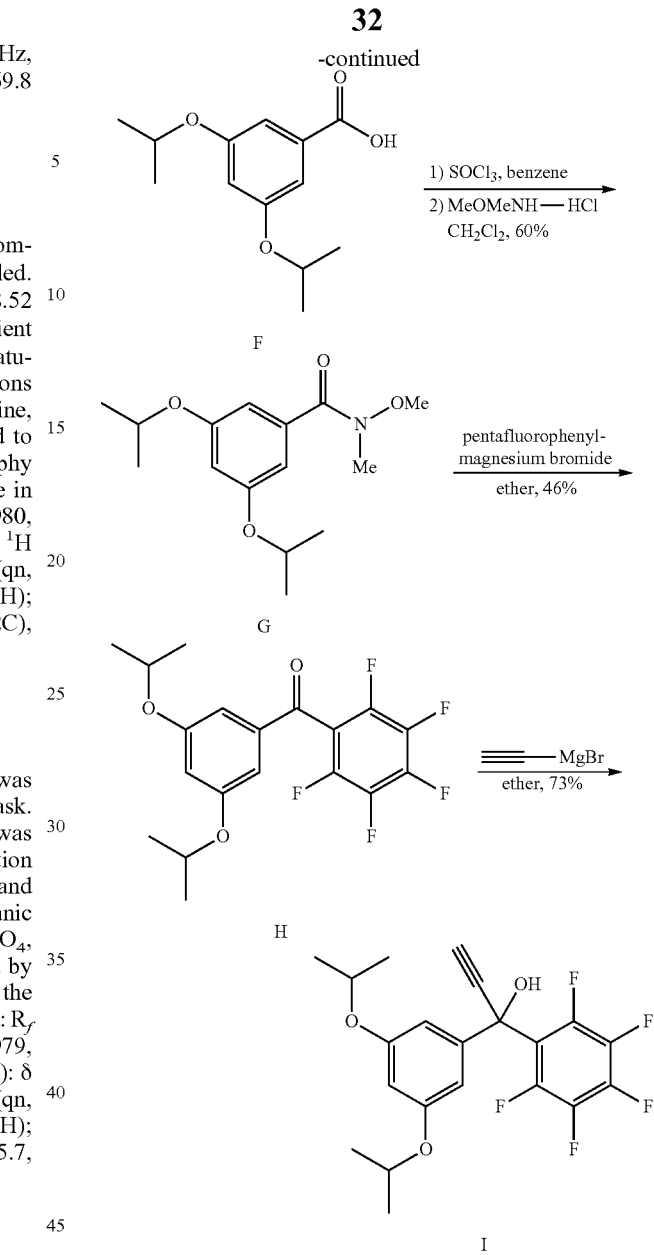

(PPh$_3$)Cl$_2$Ru(3-pentafluorophenyl-6,8-diisopropoxy-inden-1-ylidene) (J)

A 100 mL flask was charged with 1-(3,5 diisopropoxyphenyl),1-(pentafluorophenyl)-2-propyn-1-ol (compound H, 503 mg, 1.2 mmol). THF (47 mL) was then added followed by Ru(PPh$_3$)$_3$Cl$_2$ (1.17 g, 1.2 mmol) and acetyl chloride (AcCl) (86 µL in 0.86 mL THF). The reaction was refluxed for 1.5 hours after which all solvent was removed under a stream of N$_2$. The residue was suspended in 45 mL isopropanol with vigorous stirring at 40° C. for 1 hour. The resulting suspension was filtered and washed thrice with isopropanol (20 mL each time) and dried in vacuo. The crude material was loaded onto a flash column dissolved in 50% hexane/dichloromethane, and eluted with 100% dichloromethane. The solvent was removed in vacuo yielding 240 mg (23%) of the desired compound. Additional crude material was eluted with 1% and 2% MeOH in dichloromethane. This material contained PPh$_3$ and an unidentified decomposition product observed at 28.6 ppm in the $^{31}$P spectrum. The product was characterized by NMR spectra ($^1$H, $^{13}$C, and $^{31}$P). The results are as below.

$^1$H NMR (500 MHz, CD$_2$Cl$_2$, 30° C.): δ=6.0-7.0 (m, 15H), 6.62 (s, 1H), 6.56 (d, J=1 Hz, 1H), 6.50 (d, J=1.5 Hz, 1H), 5.17 (sept d, J=2, 6 Hz, 1H), 4.61 (sept, J=6 Hz, 1H), 1.75 (d, J=6 Hz, 6H), 1.36 (d, J=6 Hz, 6H); $^{19}$F NMR (250 MHz, CD$_2$Cl$_2$, 30° C.): δ=−137.39 (d, J=17.5 Hz, 2F), −154.66 (t, J=22.5 Hz, 1F), −162.6 (dt, J=6.5, 22.5 Hz, 2F); $^{31}$P NMR (250 MHz, CD$_2$Cl$_2$, 30° C.): δ=63 ppm.

Scheme 4: Synthesis of (PPh$_3$)Cl$_2$Ru(3-pentafluorophenyl-6,8-diisopropoxyinden-1-ylidene) (J)

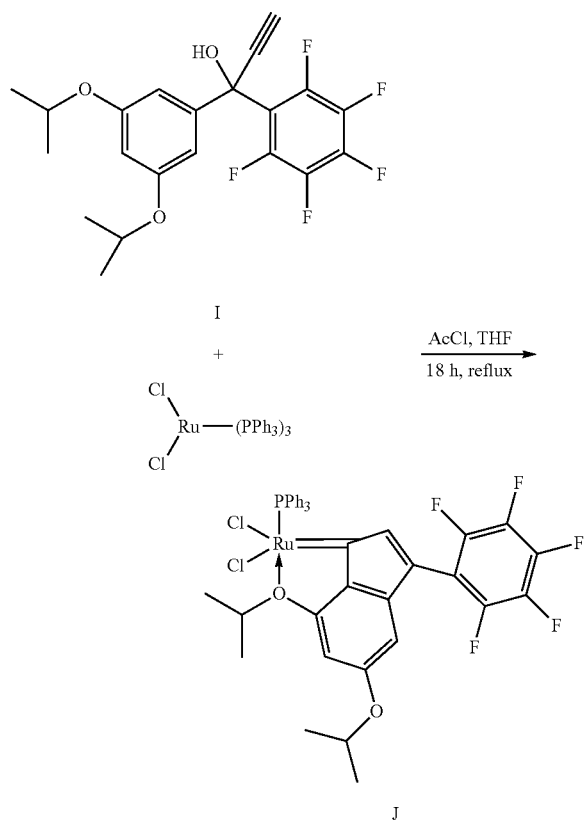

Example 3

Synthesis of (PCy$_3$)Cl$_2$Ru(3-pentafluorophenyl-6,8-diisopropoxyinden-1-ylidene) (K)

(PCy$_3$)Cl$_2$Ru(3-pentafluorophenyl-6,8-diisopropoxyinden-1-ylidene) (K)

A 10 mL vial was charged with (PPh$_3$)Cl$_2$Ru(3-pentafluorophenyl-6,8-diisopropoxyinden-1-ylidene) (compound J, 0.40 grams). Benzene (2 mLs) was then added followed by tricyclohexylphosphine (0.13 grams). The reaction was allowed to sit overnight. Excess Cu(I)Cl was added, approximately 0.50 grams. The resulting slurry was dried under vacuum, and pentane was used to extract the product (0.038 g) from the solids. The product was characterized by NMR spectra ($^1$H, $^{13}$C, and $^{31}$P). The results are as below: $^1$H NMR (250 MHz, CD$_2$Cl$_2$, 30° C.): δ=7.35 (s, 1H), 6.64 (s, 1H), 6.38 (s, 1H), 4.62 (sept, 1H), 4.26 (sept, 1H), 1.72 (d, 6H), 1.36 (d, 6H), 1.5-2.4 (m, 33H); $^{19}$F NMR (250 MHz, CD$_2$Cl$_2$, 30° C.): δ=−137.34 (d, J=17.5 Hz, 2F), −154.4 (t, J=22.5 Hz, 1F), −161.6 (dt, J=6.5, 22.5 Hz, 2F); $^{31}$P NMR (250 MHz, CD$_2$Cl$_2$, 30° C.): δ=68 ppm.

Scheme 5: Synthesis of (PCy$_3$)Cl$_2$Ru(3-pentafluorophenyl-6,8-diisopropoxyinden-1-ylidene) (K)

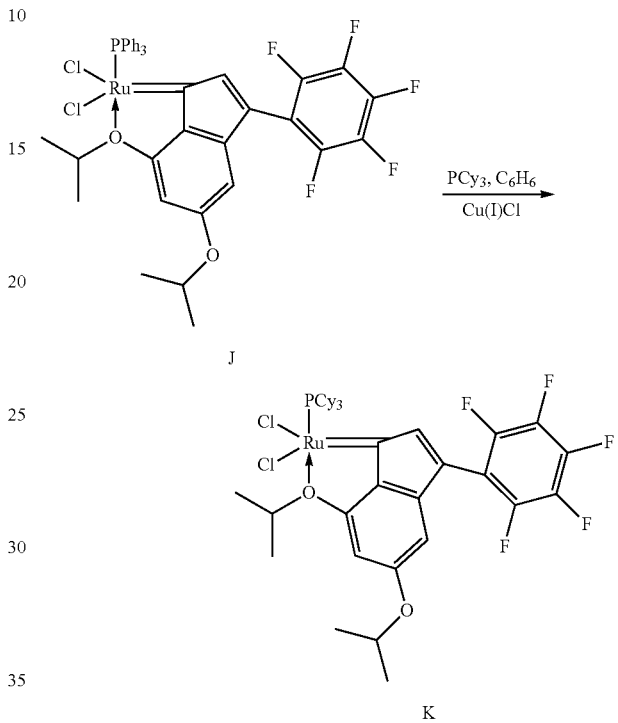

X-Ray Crystallography

X-ray quality crystals of these ruthenium complexes may be grown by dissolving the crude material in a minimal amount of a solvent such as dichloromethane and then adding an excess of another solvent of differing polarity, for example, isopropanol or hexanes. This solution is then allowed to evaporate at ambient temperature, usually under a nitrogen atmosphere, to yield crystals of the desired ruthenium complex. The crystals are usually removed from the solvent by using a glass frit. Any solid isolated from the filtrate usually contains impure crystals.

For example, X-ray quality crystals of compound J, above, were grown by dissolving the crude material in a minimal amount of dichloromethane and adding a tenfold excess of isopropanol. This solution was allowed to partially evaporate overnight at ambient temperature under a N$_2$ atmosphere to yield X-ray quality crystals.

Solid-State Structure of Compound J[(PPh$_3$)Cl$_2$Ru(3-pentafluorophenyl-6,8-diisopropoxyinden-1-ylidene)] as Determined by Single-Crystal X-Ray Diffraction Key Data and Collection Parameters RuC$_{39}$H$_{32}$PCl$_2$O$_2$F$_5$, FW 830.62, red-brown irregular, 0.6×0.3×0.06 mm, orthorhombic, a=13.268(1) A, b=20.385(2) A, c=27.051(3) A, V=7316(1) A$^3$, Pbca (#61), Z=8, d$_{calc}$=1.508, mu=6.77 cm$^{-1}$, No. obs=8342, No. variables=452, R1 (I>2σ(I))=0.115, wR2 (all reflections)=0.1826, GOF=1.137, peak=0.61, hole=−0.49, max shift/error=0.001.

Atomic coordinates and $B_{iso}/B_{eq}$

| Atom | x | y | z | $B_{eq}$ |
|---|---|---|---|---|
| Ru(1) | −0.08116(5) | 0.18381(3) | 0.63755(2) | 2.456(14) |
| Cl(1) | −0.17357(15) | 0.11104(11) | 0.58978(8) | 3.63(4) |
| Cl(2) | 0.00689(16) | 0.20266(13) | 0.70936(8) | 4.36(5) |
| P(1) | 0.05766(14) | 0.17048(10) | 0.59166(8) | 2.65(3) |
| F(1) | −0.1092(4) | 0.4978(2) | 0.6239(2) | 5.44(12) |
| F(2) | −0.0824(4) | 0.6051(2) | 0.5668(2) | 5.95(13) |
| F(3) | −0.1069(4) | 0.5980(2) | 0.4677(2) | 6.48(15) |
| F(4) | −0.1419(4) | 0.4794(2) | 0.4239(2) | 5.97(13) |
| F(5) | −0.1611(4) | 0.3709(2) | 0.48075(19) | 5.65(12) |
| O(1) | −0.2244(3) | 0.2022(2) | 0.68818(18) | 2.93(10) |
| O(2) | −0.4318(5) | 0.4008(3) | 0.7040(2) | 5.67(16) |
| C(1) | 0.0825(5) | 0.0832(4) | 0.5833(3) | 3.15(15) |
| C(2) | 0.0763(7) | 0.0422(4) | 0.6239(3) | 5.2(2) |
| C(3) | 0.0899(9) | −0.0244(5) | 0.6186(5) | 7.2(3) |
| C(4) | 0.1106(8) | −0.0518(5) | 0.5723(6) | 7.0(3) |
| C(5) | 0.1178(7) | −0.0110(5) | 0.5325(4) | 5.3(2) |
| C(6) | 0.1036(5) | 0.0560(4) | 0.5370(3) | 3.91(18) |
| C(7) | 0.1722(6) | 0.2041(4) | 0.6194(2) | 3.38(17) |
| C(8) | 0.2554(6) | 0.1642(4) | 0.6318(3) | 4.30(19) |
| C(9) | 0.3388(6) | 0.1911(7) | 0.6542(3) | 6.1(2) |
| C(10) | 0.3427(8) | 0.2556(7) | 0.6661(3) | 6.9(3) |
| C(11) | 0.2631(8) | 0.2957(6) | 0.6531(3) | 6.5(2) |
| C(12) | 0.1787(6) | 0.2691(5) | 0.6304(3) | 5.1(2) |
| C(13) | 0.0577(6) | 0.2029(3) | 0.5293(2) | 2.97(15) |
| C(14) | 0.1445(6) | 0.2284(4) | 0.5075(3) | 3.73(18) |
| C(15) | 0.1441(7) | 0.2494(4) | 0.4586(3) | 4.7(2) |
| C(16) | 0.0564(8) | 0.2462(4) | 0.4322(3) | 4.8(2) |
| C(17) | −0.0298(7) | 0.2228(4) | 0.4530(3) | 4.4(2) |
| C(18) | −0.0304(6) | 0.2011(4) | 0.5013(3) | 3.49(17) |
| C(19) | −0.1154(5) | 0.2667(3) | 0.6164(2) | 2.51(14) |
| C(20) | −0.0863(5) | 0.3180(3) | 0.5809(2) | 2.84(14) |
| C(21) | −0.1466(5) | 0.3714(3) | 0.5859(2) | 2.64(14) |
| C(22) | −0.2217(5) | 0.3587(3) | 0.6258(2) | 2.93(15) |
| C(23) | −0.2006(5) | 0.2955(3) | 0.6420(2) | 2.36(13) |
| C(24) | −0.2988(5) | 0.3940(4) | 0.6473(2) | 3.40(17) |
| C(25) | −0.3536(6) | 0.3631(4) | 0.6861(3) | 3.70(18) |
| C(26) | −0.3333(6) | 0.2997(4) | 0.7013(3) | 3.29(16) |
| C(27) | −0.2563(6) | 0.2657(3) | 0.6786(2) | 2.79(14) |
| C(28) | −0.1398(5) | 0.4311(4) | 0.5552(2) | 2.84(15) |
| C(29) | −0.1208(6) | 0.4924(4) | 0.5747(3) | 3.60(17) |
| C(30) | −0.1081(6) | 0.5485(4) | 0.5462(4) | 4.4(2) |
| C(31) | −0.1181(6) | 0.5442(4) | 0.4959(4) | 4.5(2) |
| C(32) | −0.1360(6) | 0.4848(4) | 0.4747(3) | 3.82(18) |
| C(33) | −0.1448(6) | 0.4293(4) | 0.5033(3) | 3.47(17) |
| C(34) | −0.3990(11) | 0.4325(9) | 0.7869(5) | 13.4(6) |
| C(35) | −0.4645(9) | 0.3920(5) | 0.7544(4) | 6.0(2) |
| C(36) | −0.5695(9) | 0.4154(7) | 0.7577(4) | 10.2(4) |
| C(37) | −0.2186(7) | 0.1001(4) | 0.7306(3) | 4.6(2) |
| C(38) | −0.2857(5) | 0.1582(4) | 0.7192(3) | 3.23(16) |
| C(39) | −0.3794(6) | 0.1380(4) | 0.6904(3) | 4.29(19) |

Where
$B_{eq} = 8/3 \pi^2 (U_{11}(aa^*)^2 + U_{22}(bb^*)^2 + U_{33}(cc^*)^2 + 2U_{12}(aa^*bb^*)\cos \gamma + 2U_{13}(aa^*cc^*)\cos \beta + 2U_{23}(bb^*cc^*)\cos \alpha)$.

Cross Metathesis Reactions

Representative experimental protocols for cross metathesis reactions are presented in the examples below.

Example 4

Ethylenolysis of Methyl Oleate with Ethylene Using Compound D [triphenylphosphineruthenium(3-(3,5-dimethoxyphenyl)-5,7-dimethoxy-indenylidene)]

In a 120 mL bottle, triphenylphosphineruthenium(3-(3,5-dimethoxyphenyl)-5,7-dimethoxy-indenylidene) (compound D, 5.0 mg, 6.57 µmol) was combined with 100 mL dichloromethane to make a stock solution. Some of this ruthenium catalyst compound stock solution (3.8 mL, 250 nmol) was added to a 20 mL scintillation vial along with 1 equivalent of tricyclohexylphosphine (250 nmol, added as a solution in dichloromethane). Tetradecane (0.152 g) was then added as a standard for gas chromatography analysis. The contents of the vial were transferred to a 100 mL Fisher-Porter vessel equipped with a stirring bar which was then sealed and charged with ethylene (150 psi). The bottle was then placed in an oil bath heated to 40° C. for 2 hours. The bottle was depressurized, opened and a few drops (~0.1 mL) of ethyl vinyl ether were added prior to analysis. 1-decene and methyl-9-decenoate yields corresponded to 1800 turnovers of decene per equivalent of ruthenium.

Example 5

Ethylenolysis of Methyl Oleate Using Compound K, $(PCy_3)Cl_2Ru(3$-pentafluorophenyl-6,8-diisopropoxy-inden-1-ylidene)

The ethylenolysis of methyl oleate was used as a test to determine the activity of $(PCy_3)Cl_2Ru(3$-pentafluorophenyl-6,8-diisopropoxyinden-1-ylidene). A catalyst compound stock solution (0.1379 mM) was made by dissolving the catalyst compound in anhydrous dichloromethane. Methyl oleate (0.87 g, 1.0 mL), catalyst compound stock solution (0.906 g), dichloromethane (4.12 g), and tetradecane (0.152 g) as an internal standard were placed in a Fisher-Porter bottle equipped with a stir bar. The vessel was then filled with ethylene to 150 psig and placed in an oil bath heated to 40° C. for 3 hours. The vessel was then depressurized and 5 drops ethyl vinyl ether added to stop the reaction. A sample was analyzed by gas chromatography. The cross-metathesis reaction yielded 18.5% 1-decene and methyl-9-decenoate with 99% selectivity 1-decene and methyl-9-decenoate yields corresponded to 4300 turnovers of decene per equivalent of ruthenium.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications may be made without departing from the spirit and scope of the invention. Accordingly, it is not intended that the invention be limited thereby. Likewise, the term "comprising" is considered synonymous with the term "including" for purposes of Australian law.

The invention claimed is:

1. A process to produce $C_4$ to $C_{24}$ linear alpha-olefin comprising contacting a feed material with an alkene selected from the group consisting of ethylene, propylene butene, pentene, hexene, heptene, octene, nonene, and mixtures thereof and a metathesis catalyst compound represented by the formula:

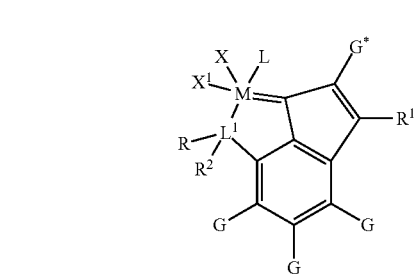

wherein

M is a Group 8 metal from the Periodic Table of the Elements;

X and $X^1$ are anionic ligands;

L is a neutral two electron donor;

$L^1$ is P;

R is a $C_1$ to $C_{30}$ hydrocarbyl or a $C_1$ to $C_{30}$ substituted hydrocarbyl;

G* is selected from the group consisting of hydrogen, a $C_1$ to $C_{30}$ hydrocarbyl, and a $C_1$ to $C_{30}$ substituted hydrocarbyl;

$R^1$ is selected from the group consisting of hydrogen, a $C_1$ to $C_{30}$ hydrocarbyl, and a $C_1$ to $C_{30}$ substituted hydrocarbyl;

$R^2$ is selected form the Group consisting of hydrogen, $C_1$ to $C_{30}$ hydrocarbyl, and $C_1$ to $C_{30}$ substituted hydrocarbyl; and G is independently selected from the group consisting of hydrogen, halogen, $C_1$ to $C_{30}$ hydrocarbyls and $C_1$ to $C_{30}$ substituted hydrocarbyls and wherein the alpha olefin produced has at least one more carbon atom than the alkene, wherein the feed material is a triacylglyceride, fatty acid, fatty acid alkyl ester and fatty acid ester derived from seed oil.

2. The catalyst compound of claim 1, wherein M is Ru.

3. The catalyst compound of claim 1, wherein X and $X^1$ are independently selected from the group consisting of halides, alkoxides, aryloxides, and alkyl sulfonates.

4. The catalyst compound of claim 1, wherein at least one of X and $X^1$ is a chloride.

5. The catalyst compound of claim 1, wherein $L^1$ is N.

6. The catalyst compound of claim 1, wherein L is selected from the group consisting of a phosphine, an N-heterocyclic carbene, and a cyclic alkyl amino carbene.

7. The catalyst compound of claim 1, wherein G* is selected from the group consisting of hydrogen, an alkyl, and a substituted alkyl.

8. The catalyst compound of claim 1, wherein each G is independently, a $C_1$ to $C_{30}$ substituted or unsubstituted alkyl, or a substituted or unsubstituted $C_4$ to $C_{30}$ aryl.

9. The catalyst compound of claim 1, wherein $R^1$ is a methoxy substituted phenyl.

10. The catalyst compound of claim 1, wherein L and X are joined to form a multidentate monoanionic group or a dianionic group and form a single ring of up to 30 non-hydrogen atoms or a multinuclear ring system of up to 30 non-hydrogen atoms.

11. A process to produce alpha-olefin comprising contacting an unsaturated fatty acid with an alkene and the catalyst compound of claim 1.

12. A process to produce alpha-olefin comprising contacting a triacylglyceride with the catalyst compound of claim 1.

13. A process to produce alpha-olefin comprising contacting an unsaturated fatty acid ester or unsaturated fatty acid alkyl ester with an alkene and the catalyst compound of claim 1.

14. The process claim 13, wherein the alpha olefin is a linear alpha-olefin having 4 to 24 carbon atoms.

15. The process of claim 13, wherein the alkene is ethylene, propylene, butene, hexene or octene.

16. The process of claim 13, where the fatty acid alkyl ester is a fatty acid methyl ester.

17. The process of claim 13, wherein the alpha-olefin is butene-1, decene-1, or heptene-1.

18. The process of claim 13, wherein the alpha-olefin is butene-1, decene-1, and heptene-1.

19. A process to produce alpha-olefin comprising contacting an unsaturated fatty acid ester and unsaturated fatty acid alkyl ester with an alkene and the catalyst compound of claim 1.

20. A process to produce $C_4$ to $C_{24}$ linear alpha-olefin comprising contacting a feed material with an alkene selected from the group consisting of ethylene, propylene butene, pentene, hexene, heptene, octene, nonene, and mixtures thereof and a metathesis catalyst compound represented by the formula:

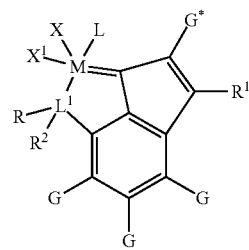

wherein

M is a Group 8 metal from the Periodic Table of the Elements;

X and $X^1$ are anionic ligands;

L is a neutral two electron donor;

$L^1$ is P;

R is a $C_1$ to $C_{30}$ hydrocarbyl or a $C_1$ to $C_{30}$ substituted hydrocarbyl;

G* is selected from the group consisting of hydrogen, a $C_1$ to $C_{30}$ hydrocarbyl, and a $C_1$ to $C_{30}$ substituted hydrocarbyl;

$R^1$ is selected from the group consisting of hydrogen, a $C_1$ to $C_{30}$ hydrocarbyl, and a $C_1$ to $C_{30}$ substituted hydrocarbyl;

$R^2$ is selected form the Group consisting of hydrogen, $C_1$ to $C_{30}$ hydrocarbyl, and $C_1$ to $C_{30}$ substituted hydrocarbyl; and G is independently selected from the group consisting of hydrogen, halogen, $C_1$ to $C_{30}$ hydrocarbyls and $C_1$ to $C_{30}$ substituted hydrocarbyls and wherein the alpha olefin produced has at least one more carbon atom than the alkene, wherein the feed material is a triacylglyceride, fatty acid, fatty acid alkyl ester and fatty acid ester derived from seed oil.

21. The process of claim 20, wherein the feed material is a seed oil which is selected from the group consisting of canola oil, corn oil, soybean oil, rapeseed oil, algae oil, peanut oil, mustard oil, sunflower oil, tung oil, perilla oil, grapeseed oil, linseed oil, safflower oil, pumpkin oil, palm oil, Jathropa oil, high-oleic soybean oil, high-oleic safflower oil, high-oleic sunflower oil, mixtures of animal and vegetable fats and oils, castor bean oil, dehydrated castor bean oil, cucumber oil, poppyseed oil, flaxseed oil, lesquerella oil, walnut oil, cottonseed oil, meadowfoam, tuna oil, sesame oils, and mixtures thereof.

22. The process of claim 20, wherein the feed material is selected from the group consisting of palm oil and algae oil.

23. A process to produce $C_4$ to $C_{24}$ linear alpha-olefin comprising contacting a feed material with an alkene selected from the group consisting of ethylene, propylene butene, pentene, hexene, heptene, octene, nonene, and mixtures thereof and a metathesis catalyst compound represented by the formula:

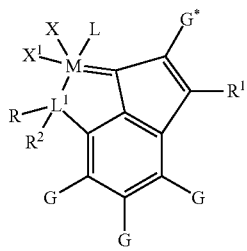

wherein

M is a Group 8 metal from the Periodic Table of the Elements;

X and $X^1$ are anionic ligands;

L is a neutral two electron donor;

$L^1$ is P;

R is a $C_1$ to $C_{30}$ hydrocarbyl or a $C_1$ to $C_{30}$ substituted hydrocarbyl;

G* is selected from the group consisting of hydrogen, a $C_1$ to $C_{30}$ hydrocarbyl, and a $C_1$ to $C_{30}$ substituted hydrocarbyl;

$R^1$ is selected from the group consisting of hydrogen, a $C_1$ to $C_{30}$ hydrocarbyl, and a $C_1$ to $C_{30}$ substituted hydrocarbyl;

$R^2$ is selected form the Group consisting of hydrogen, $C_1$ to $C_{30}$ hydrocarbyl, and $C_1$ to $C_{30}$ substituted hydrocarbyl; and G is independently selected from the group consisting of hydrogen, halogen, $C_1$ to $C_{30}$ hydrocarbyls and $C_1$ to $C_{30}$ substituted hydrocarbyls and wherein the alpha olefin produced has at least one more carbon atom than the alkene, wherein the feed material is a triacylglyceride, fatty acid, fatty acid alkyl ester and fatty acid ester derived from seed oil.

24. The process of claim 23, wherein the triacylglyceride is contacted with alcohol and converted to an fatty acid ester or fatty acid alkyl ester prior to contacting with the catalyst compound.

25. The process of claim 23, wherein the triacylglyceride is contacted with water and converted to a fatty acid prior to contacting with the catalyst compound.

26. The process of claim 23, wherein the productivity of the process is at least 200 g of linear alpha-olefin per mmol of catalyst per hour.

27. The process of claim 23, wherein the selectivity of the process is at least 20 wt % linear alpha-olefin, based upon the weight to the material exiting the reactor.

28. The process of claim 23, wherein the turnover number, defined as the moles of alpha olefin formed per mol of catalyst, of the process is at least 10,000.

29. The process of claim 23, wherein the yield, when converting unsaturated fatty acids, unsaturated fatty acid esters, unsaturated fatty acid alkyl esters or mixtures thereof, is 30% or more, said yield being defined as defined as the moles of alpha olefin formed per mol of unsaturated fatty acids, unsaturated fatty acid esters, unsaturated fatty acid alkyl esters, or mixtures thereof introduced into the reactor.

30. The process of claim 29, wherein the yield is 60% or more.

31. The process of claim 23, wherein the yield, when converting triacylglycerides as represented in the formula below, is 30% or more, said yield being defined as the moles of alpha olefin formed divided by (the moles of unsaturated $R^a$+moles of unsaturated $R^b$+moles of unsaturated $R^c$) introduced into the reactor,

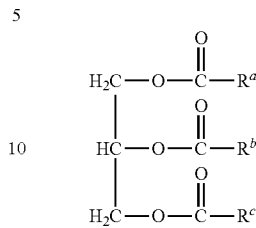

where $R^a$, $R^b$, and $R^c$ each, independently, represent a saturated or unsaturated hydrocarbon chain.

32. A process to produce $C_4$ to $C_{24}$ linear alpha-olefin comprising contacting a feed material with an alkene selected from the group consisting of ethylene, propylene butene, pentene, hexene, heptene, octene, nonene, and mixtures thereof and a metathesis catalyst compound represented by the formula:

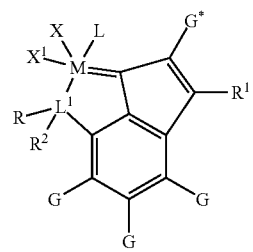

wherein

M is a Group 8 metal from the Periodic Table of the Elements;

X and $X^1$ are anionic ligands;

L is a neutral two electron donor;

$L^1$ is P;

R is a $C_1$ to $C_{30}$ hydrocarbyl or a $C_1$ to $C_{30}$ substituted hydrocarbyl;

G* is selected from the group consisting of hydrogen, a $C_1$ to $C_{30}$ hydrocarbyl, and a $C_1$ to $C_{30}$ substituted hydrocarbyl;

$R^1$ is selected from the group consisting of hydrogen, a $C_1$ to $C_{30}$ hydrocarbyl, and a $C_1$ to $C_{30}$ substituted hydrocarbyl;

$R^2$ is selected form the Group consisting of hydrogen, $C_1$ to $C_{30}$ hydrocarbyl, and $C_1$ to $C_{30}$ substituted hydrocarbyl; and G is independently selected from the group consisting of hydrogen, halogen, $C_1$ to $C_{30}$ hydrocarbyls and $C_1$ to $C_{30}$ substituted hydrocarbyls and wherein the alpha olefin produced has at least one more carbon atom than the alkene, wherein the feed material is a triacylglyceride, fatty acid, fatty acid alkyl ester and fatty acid ester derived from seed oil.

33. A process to produce $C_4$ to $C_{24}$ linear alpha-olefin comprising contacting a feed material with an alkene selected from the group consisting of ethylene, propylene butene, pentene, hexene, heptene, octene, nonene, and mixtures thereof and a metathesis catalyst compound represented by the formula:

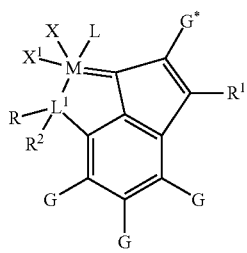

wherein

M is a Group 8 metal from the Periodic Table of the Elements;

X and $X^1$ are anionic ligands;

L is a neutral two electron donor;

$L^1$ is P;

R is a $C_1$ to $C_{30}$ hydrocarbyl or a $C_1$ to $C_{30}$ substituted hydrocarbyl;

G* is selected from the group consisting of hydrogen, a $C_1$ to $C_{30}$ hydrocarbyl, and a $C_1$ to $C_{30}$ substituted hydrocarbyl;

$R^1$ is selected from the group consisting of hydrogen, a $C_1$ to $C_{30}$ hydrocarbyl, and a $C_1$ to $C_{30}$ substituted hydrocarbyl;

$R^2$ is selected form the Group consisting of hydrogen, $C_1$ to $C_{30}$ hydrocarbyl, and $C_1$ to $C_{30}$ substituted hydrocarbyl; and G is independently selected from the group consisting of hydrogen, halogen, $C_1$ to $C_{30}$ hydrocarbyls and $C_1$ to $C_{30}$ substituted hydrocarbyls and wherein the alpha olefin produced has at least one more carbon atom than the alkene, wherein the feed material is a triacylglyceride, fatty acid, fatty acid alkyl ester or fatty acid ester derived from seed oil.

34. The process of claim 33, wherein the alkene is ethylene; the alpha olefin is 1-butene, 1-heptene, or 1-decene; and the feed material is a fatty acid methyl ester or fatty acid ester.

35. The process of claim 33, wherein the alkene is ethylene; the alpha olefin is 1-butene, 1-heptene, and 1-decene; and the feed material is a fatty acid methyl ester and fatty acid ester.

36. The process of claim 33, wherein the alkene is ethylene; the alpha olefin is 1-butene, 1-heptene, and 1-decene; and the feed material is a fatty acid methyl ester or fatty acid ester.

37. The process of claim 33, wherein the alkene is ethylene; the alpha olefin is 1-butene, 1-heptene, or 1-decene; and the feed material is a fatty acid methyl ester and fatty acid ester.

38. A process to produce $C_4$ to $C_{24}$ linear alpha-olefin comprising contacting a feed material with an alkene selected from the group consisting of ethylene, propylene butene, pentene, hexene, heptene, octene, nonene, and mixtures thereof and a metathesis catalyst compound represented by the formula:

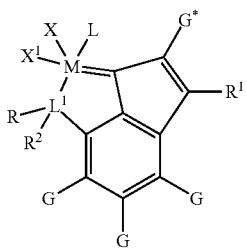

wherein

M is a Group 8 metal from the Periodic Table of the Elements;

X and $X^1$ are anionic ligands;

L is a neutral two electron donor;

$L^1$ is P;

R is a $C_1$ to $C_{30}$ hydrocarbyl or a $C_1$ to $C_{30}$ substituted hydrocarbyl;

G* is selected from the group consisting of hydrogen, a $C_1$ to $C_{30}$ hydrocarbyl, and a $C_1$ to $C_{30}$ substituted hydrocarbyl;

$R^1$ is selected from the group consisting of hydrogen, a $C_1$ to $C_{30}$ hydrocarbyl, and a $C_1$ to $C_{30}$ substituted hydrocarbyl;

$R^2$ is selected form the Group consisting of hydrogen, $C_1$ to $C_{30}$ hydrocarbyl, and $C_1$ to $C_{30}$ substituted hydrocarbyl; and G is independently selected from the group consisting of hydrogen, halogen, $C_1$ to $C_{30}$ hydrocarbyls and $C_1$ to $C_{30}$ substituted hydrocarbyls and wherein the alpha olefin produced has at least one more carbon atom than the alkene, wherein the feed material is a triacylglyceride, fatty acid, fatty acid alkyl ester and fatty acid ester derived from seed oil.

* * * * *